United States Patent
Brown et al.

(12) 
(10) Patent No.: US 6,416,754 B1
(45) Date of Patent: Jul. 9, 2002

(54) ANAEROBE TARGETED ENZYME-MEDIATED PRODRUG THERAPY

(75) Inventors: John Martin Brown, Redwood City, CA (US); Nigel P. Minton, Salisbury (GB); Amato Giaccia, Stanford, CA (US)

(73) Assignees: The Board of Trustees of the Leland Stanford Junior University; Microbiological Research Authority (MRA) acting through the Centre for Applied Microbiology and Research (CAMR) (GB)

( * ) Notice: Subject to any disclaimer, the term of this patent is extended or adjusted under 35 U.S.C. 154(b) by 0 days.

(21) Appl. No.: 08/686,502

(22) Filed: Jul. 23, 1996

Related U.S. Application Data

(63) Continuation of application No. 08/465,932, filed on Jun. 6, 1995, now abandoned, which is a continuation of application No. 08/227,313, filed on Apr. 13, 1994, now abandoned, which is a continuation of application No. 08/206,430, filed on Mar. 3, 1994, now abandoned.

(51) Int. Cl.$^7$ ............................................. A61K 48/00
(52) U.S. Cl. ............................... 424/93.21; 435/320.1; 435/252.3; 435/252.7; 435/191; 435/227; 435/206; 435/325; 435/357; 435/366; 435/367; 536/23.2; 514/44
(58) Field of Search ........................ 435/320.1, 252.3, 435/191, 206, 227, 252.7, 325, 357, 366, 367; 424/93.21; 536/23.2; 514/44

(56) References Cited

U.S. PATENT DOCUMENTS 5,633,158 A * 5/1997 Anlezark et al. ........... 435/189

FOREIGN PATENT DOCUMENTS

| DE | 228301 | 10/1985 |
| WO | WO 93/08288 | 4/1993 |

OTHER PUBLICATIONS

Boyd, "The future of new drug development" *Current Therapy in Oncology* (1992), Decker et al., eds. pp. 11–22.
Jain, "Delivery of novel therapeutic agents in tumors: physiological barriers and strategies" *J. Natl. Cancer Inst.* (1989) 81:570–576.
Bagshawe, "Towards generating cytotoxic agents at cancer sites" *Br. J. Cancer* (1989) 60:275–281.
Senter, "Activation of prodrugs by antibody–enzyme conjugates: a new approach to cancer therapy" *FASEB J.* (1990) 4:188–193.
Antoniw et al., "Disposition of the prodrug 4–(bis (2–chloroethyl) amino) benzoyl–L–glutamic acid and its active parent drug in mice" *Br. J. Cancer* (1990) 62:909–914.
Fitzgerald et al., "Pseudomonas exotoxin: recombinant conjugates as therapeutic agents" *Biochem. Soc. Trans.* (1992) 20:731–734.
Rosenberg, "Gene therapy for cancer" *JAMA* (1992) 268:2416–2419.
Schlechte et al., "Recombinant plasmid DNA variation of clostridium oncolyticum—model experiments of cancerostatic gene transfer" *Zbl. Bakt. Hyg.* (1988) A268:347–356. An English abstract is included on p. 347 of this publication.
Mullen et al., "Transfer of the bacterial gene for cytosine deaminase to mammalian cells confers lethal sensitivity to 5–fluorocytosine: a negative selection system" *Proc. Natl. Acad. Sci. USA* (1992) 89:33–37.
Thiele et al., "Oncolysis by *Clostridia*. IV. Effect of nonpathogenic clostridial spores in normal and pathological tissue" *Cancer Res.* (1964) 24:234–238.
Oultram et al., "Introduction of plasmids into whole cells of *Clostridium acetobutylicum* by electroporation" *FEMS Microbiol. Lett.* (1988) 56:83–88.
Graves et al., "Cloning and nucleotide sequence determination of the *Clostridium pasteurianum* ferredoxin gene" *Proc. Natl. Acad. Sci. USA* (1985) 82:1653–1657.
Anlezark et al., "The bioactivation of 5–(Aziridin–1–YL)–2, 4–Dinitrobenzamide (CB1954)–I" *Biochem. Pharmacol.* (1992) 44:2289–2295.
Bryant et al., "Cloning, nucleotide sequence, and expression of the nitroreductase gene from *Enterobacter cloacae*" *J. Biol. Chem.* (1991) 266:4126–4130.
Watanabe et al., "Nucleotide sequence of *Salmonella typhimurium* nitroreductase gene" *Nucleic Acid Res.* (1990) 18:1059.

* cited by examiner

*Primary Examiner*—Christopher S. F. Low
(74) *Attorney, Agent, or Firm*—Perkins Coie LLP

(57) ABSTRACT

A genetically-engineered anaerobic organism is provided which, under anaerobic conditions present in a solid tumor, produces an enzyme capable of catalyzing the conversion of a prodrug to its highly cytotoxic product in situ and methods of treating tumors using same.

3 Claims, 13 Drawing Sheets

```
              MboI
GAATTCCCCG GATCGAGATA GTATATGATG CATATTCTTT AAATATAGAT   50
EcoRI

AAAGTTATAG AAGCAATAGA AGATTTAGGA TTTACTGTAA TATAAATTAC  100
     -35       promoter      -10
ACTTTTAAAA AGTTTAAAAA CATGATACAA TAAGTTATGG TtGGAATTGT  150
  lac operator                        ribosome binding site
TATCCGCTCA CAATTCCAAC TTATGATTAA AATTTTAAGGA GGTGTATTT  200 cat  ATG  ← START CODON lacZ'

NdeI
```

Fig. 9

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 206 base pairs
      (B) TYPE: nucleic acid
      (C) STRANDEDNESS: unknown
      (D) TOPOLOGY: unknown (ii) MOLECULE TYPE: DNA (iii) HYPOTHETICAL: NO (iv) ANTI-SENSE: NO

```
       (vi) ORIGINAL SOURCE:
             (C) INDIVIDUAL ISOLATE: Sequence in Fig. 9

(xi) SEQUENCE DESCRIPTION: SEQ ID NO:1:

GAATTCCCCG GATCGAGATA GTATATGATG CATATTCTTT AAATATAGAT AAAGTTATAG        60

AAGCAATAGA AGATTTAGGA TTTACTGTAA TATAAATTAC ACTTTTAAAA AGTTTAAAAA       120

CATGATACAA TAAGTTATGG TTGGAATTGT TATCCGCTCA CAATTCCAAC TTATGATTAA       180

AATTTTAAGG AGGTGTATTT CATATG                                           206
```

ANAEROBE TARGETED ENZYME-MEDIATED PRODRUG THERAPY

CROSS-REFERENCE TO RELATED APPLICATIONS

This application is a continuation of U.S. Ser. No. 08/465,932, filed Jun. 6, 1995, now abandoned, which is a continuation of U.S. Ser. No. 08/227,313, filed Apr. 13, 1994, now abandoned, which is a continuation of U.S. Ser.No. 08/206,430, filed Mar. 3, 1994, now abandoned, all of which are incorporated herein by reference.

TECHNICAL FIELD

This invention relates to a genetically-engineered anaerobic organism which, under anaerobic conditions present in a solid tumor, produces an enzyme capable of catalyzing the conversion of a prodrug to its highly cytotoxic product in situ and methods of treating tumors using same.

BACKGROUND

Despite the success of modern chemotherapy in curing certain types of leukemia and lymphoma and a few other relatively rare cancers, few of the current anticancer drugs have much useful clinical activity against the most common forms of cancer. These poorly responsive cancers are typically solid tumors comprising both proliferating and non-proliferating cells. Typically, the anticancer drugs used today are effective predominantly against rapidly proliferating tumor cells, and are toxic to rapidly proliferating normal tissues. Two general approaches are currently being pursued to overcome this problem. First, there is an intensive search for new drugs with selectivity against individual types of cancer cells. For example, the National Cancer Institute is currently screening some 20,000 compounds per year against a panel of 60 human tumor cells lines (Boyd, M. R. "The Future of New Drug Development," In: *CURRENT THERAPY IN ONCOLOGY* pp 11–22 (B. C. Decker, Inc., Neiderhuber, J. E., eds. Philadelphia 1992)). A second approach is that of targeting new or,existing drugs specifically to the tumor. Many of these approaches rely on monoclonal antibodies (Mabs) to carry a drug or toxin to the tumor. A major problem confronting most of these strategies, however, is tumor cell heterogeneity and inability to deliver the antibody conjugates to every tumor cell (Jain, R. K., (1989) *J. Natl. Cancer Inst.* 81:570–576). One way of overcoming this problem is the use of enzyme-antibody conjugates which activate prodrugs to form diffusible cytotoxins (Bagshawe, K. D., (1989) *Br. J. Cancer* 60:275–281). This approach has been called antibody-directed enzyme prodrug therapy (ADEPT). The two-step ADEPT process requires the conjugation of a suitable enzyme to a monoclonal antibody which localizes the enzyme to the tumor. When most of the nonbound antibody-enzyme conjugate has been cleared, a prodrug is administered which can be activated by the enzyme to a cytotoxic species (Bagshawe, K. D., supra; Senter, P. D. (1990) *FASEB J.* 4:188–193). Though the ADEPT strategy is promising, it has a number of problems. First, the large majority of the MAb-enzyme conjugates do not localize in the tumor, and studies have shown that concentrations of the active drug in normal tissues can be greater than in the tumor (Antoniw et al., (1990) *Br. J. Cancer* 62:909–914). Also, MAbs of high enough specificity are not available for many tumors.

Other targeting approaches include the use of recombinant toxins, such as growth factors fused to a bacterial toxin (Fitzgerald et al., (1992) *Biochem. Soc. Trans.* 20:731–734), and the use of tumor-infiltrating lymphocytes genetically engineered to produce a protein such as tumor necrosis factor (TNF) (Rosenberg, S. A., (1992) *JAMA* 268:2416–2419). No reports of improved activity of any of these targeting strategies has yet appeared.

In another approach, a gene for the cancerostatic polypeptide Colicin E3 was introduced into the uncharacterized mixture of endogenous plasmids in *C. oncolyticum* (*C. butyricum* M-55, renamed because of its oncolytic activity) (Schlechte, H, and B. Albe, (1988) *Zbl. Bakt. Hyg.* A 268:347–356). This approach, however, was unsuccessful. They were unable to show that these recombinants were expressing active protein. Though this approach might ultimately lead to a clostridial strain expressing an anticancer polypeptide, the major drawbacks of this strategy are first, that the anticancer agent must be a protein rather than a low molecular weight anticancer drug which presently constitute all chemotherapeutic agents, and, second, the inability to control the production of the toxic product.

Accordingly, a need exists for a means for selectively targeting a toxic chemotherapeutic agent to solid tumor tissue without exposing healthy tissue to the agent.

DESCRIPTION OF THE INVENTION

This invention is based on the finding that an anaerobic microorganism can be genetically engineered to produce an enzyme that can catalyze the conversion of a non toxic prodrug to a highly cytotoxic chemotherapeutic agent. When injected into a subject, the genetically engineered microorganism will proliferate and produce the enzyme exclusively in the hypoxic/necrotic regions of a tumor in an otherwise healthy individual. The tumor-bearing individual is treated systemically with a non toxic prodrug which is converted to the highly toxic counterpart by the enzyme which, due to the anaerobic nature of the microorganism producing it, will only be present in the hypoxic/necrotic regions of the tumor. Since the enzyme is localized to the tumor, the generation of the toxic product is also localized to the tumor thus preventing the systemic toxicity associated with direct administration of the toxic chemotherapeutic agent but providing for the diffusion of the enzyme, prodrug and toxic product throughout the tumor.

Accordingly, one aspect of the invention is a vector expressed in obligate anaerobes for the production of an enzyme capable of converting a non toxic prodrug to a toxic chemotherapeutic agent. A member of the genus Clostridium is a preferred anaerobe. *Clostridium acetobutylicum* is a particularly preferred anaerobe. The enzymes nitroreductase, B-glucuronidase and cytosine deaminase are preferred enzymes. A clostridial vector comprising the ntr gene encoding *E. coli* B nitroreductase. (NTR) and the promoter and RBS of the ferredoxin (Fd) gene of *Clostridium pasteurianum* for the expression of nitroreductase in *Clostridium acetobutylicum* is a preferred embodiment of the present invention. CB1954, 5-fluorocytosine, and glucuronides of epirubicin, 5-fluorouracil and 4-hydroxycyclophosphamide are preferred prodrugs.

Another aspect of the invention is a method of targeting a toxic chemotherapeutic agent to a tumor in a tumor-bearing individual comprising the steps of:

a) administering an effective amount of a genetically engineered anaerobic microorganism capable of proliferating and producing an enzyme in the hypoxic/necrotic environment of a tumor to said individual; and then b) systemically administering a prodrug which is converted at the site of the tumor to the toxic chemotherapeutic agent by the enzyme produced by the microorganism. A method comprising administering an effective amount of *Clostridium acetobutylicum* genetically engineered to produce *E. coli* B nitroreductase (NTR) and then administering the prodrug CB1954 is a preferred method. Other preferred methods involve administering *Clostridium acetobutylicum* genetically engineered to produce β-glucuronidase or cytosine deaminase and then administering prodrugs comprising glucuronides of epirubicin, 5-fluorouracil, and 4-hydroxycyclophosphamide, or 5-fluorocytosine, respectively.

BRIEF DESCRIPTION OF THE DRAWINGS

FIG. 5A is an artist rendering of a nondenaturing polyacrylamide gel in which 50 μg of EMT6 tumor lysate has been mixed with decreasing amounts (5 μg to 250 ng) oc *C. acetobutylicum* expressing NTR activity and stained for NTR-like activity. FIG. 5B is an artist rendering of a Western blot stained as described in the Methods section using antibody raised against *E. coli* NTR. The lanes contain molecular weight markers, 1 ng purified NTR as standard, and 25 μg protein of EMT6 tumor lysates derived from tumor-bearing mice 4 days following i.v. injection of saline or $10^8$ spores from wild type or NTR-expressing *C. acetobutylicum*.

FIG. 9 illustrates the nucleotide sequence (SEQ ID NO:1) of the modified *Clostridium pasteurianum* Fd gene promoter. One of the MboI sites employed in the original cloning of the 604 bp fragment has been bracketed. The nucleotides shown 5' to this MboI site, including the EcoRI site, are derived from M13mp7. The −35 and −10 promoter motifs are over lined, and the ribosome binding site and inserted lac operator motif have been boxed. Nucleotides created by SDM are shown in lower case. The boxed ATG corresponds to that of the original Fd structural gene, but becomes that of the lacZ' gene in all plasmids described in FIGS. 10–13.

MODES FOR CARRYING OUT THE INVENTION

Genetically Engineered Anaerobic Microorganism

The ability of spores of the genus Clostridium to germinate in necrotic tissues is widely known. Tetanus and gas gangrene, for example, result from successful colonization of necrotic tissue by pathogenic strains of these organisms. In the absence of necrotic tissue, however, these organisms are inert. In 1955, Malmgren and Flanagan, *Cancer Res.* 15:473, showed that tumor-bearing mice died of tetanus within 48 hours of intravenous injection of *C. tetani* spores, whereas non tumor-bearing animals were unaffected. Microscopic observations confirmed that vegetative forms were localized solely in the tumor tissue. Möse and Möse ((1959) *Z. Krebsforsch* 63:63–74 and (1964) *Cancer Res.* 24:212–216), later reported that a nonpathogenic clostridial strain, *C. butyricum* M-55, localized and germinated in solid Ehrlich tumors, causing extensive lysis without concomitant effect on normal tissues. These observations have been confirmed and extended by a number of investigators using tumors in mice, rats, hamsters, rabbits, and man (Carey et al. (1967) *Europ. J. Cancer* 3: 37–46; Engelbart, K, and D. Gericke (1964) *Cancer Res.* 24:239–243; Thiel et al. (1964) *Oncolysis by clostridia. IV. Effects of clostridia and chemotherapeutic agents on rodent tumors* 242).

It was a common finding, particularly with the very large tumors used in the experiments performed in the early 1960's that the extensive lysis of the tumor often produced death of the animal, presumably due to toxins released into the blood stream from the clostridia or the lysed cells.

However, with mouse tumors less than 1 cm diameter, lysis does not lead to animal death. The present invention does not require cellular lysis for activity. Indeed, it is advantageous to stop the reaction before extensive lysis has occurred, so as to avoid these potential problems.

Nonpathogenic strains of clostridia which allow genetic manipulations within the present invention include, but are not limited to, *C. acetobutylicum*. This microorganism has a the long history, dating back to World War I, of use in producing acetone and butanol, and more recently has been manipulated molecularly to exploit its biotechnological potential (Minton et al., Vector Systems for the genetic analysis of *Clostridium acetobutylicum*, 187–201, In: *CLINICAL AND MOLECULAR ASPECTS OF ANAEROBES* (Borriello, S. P., eds., Wrightson Biomedical Publishing, 1993). *C. acetobutylicum* germinates in tumor tissue, and tumor lysis has been reported for this strain (Mose, J. R. and G. Mose (1964) *Cancer Res*. 24:212–216). Antitumor activity is optimally produced by spores rather than the vegetative form (Mose and Mose, supra), and *C. acetobutylicum* produces spores under the conditions present in the targeted tumor. The nonpathogenic clostridial strain, *C. acetobutylicum* strain NCIB 8052, is a preferred embodiment of the present invention.

Enzyme—Prodrug Combinations (a) Nitroreductase with CB1954

Figure 1:
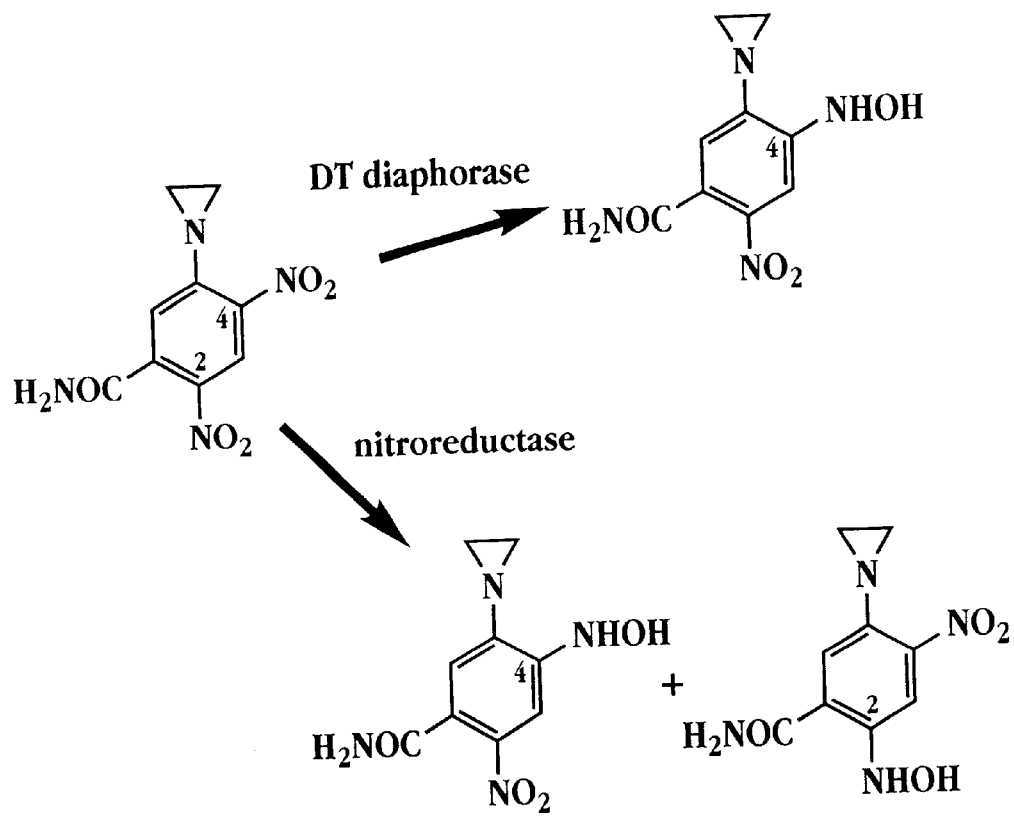
FIG. 1 shows the formula of CB1954 and the products formed by its reduction by either Walker DT diaphorase or *E. coli* nitroreductase (60).

The monofunctional alkylating agent, CB1954 (5-[aziridin-1-yl]-2,4-dinitrobenzamide), was synthesized almost 25 years ago at the Chester Beatty Institute (Kim et al. (1993) *Rad. Res*. 135:in press). It was shown to have potent activity against the Walker 256 rat carcinoma in vivo (Cobb et al. (1969) *Biochem. Pharmacol*. 18:1519–1527) and on Walker carcinoma cells in vitro (Roberts et al. (1986) *Biochem. Biophys. Res. Commun*. 140:1073–1078). However, it has poor activity against a range of mouse and human tumor cell lines (Boland et al. (1991) *Biochem. Pharmacol*. 41:867–875; Workman et al. (1986) *Cancer Chemother. Pharmacol*. 16:9–14). The extreme toxicity of the drug to Walker tumor cells was demonstrated to be the result of its conversion to a bifunctional alkylating agent which caused DNA interstrand crosslinks in these cells (Roberts et al., supra). Subsequently, the toxic bifunctional alkylating agent was identified as the 4-hydroxylamine metabolite of CB1954, which was formed by a DT-diaphorase enzyme in Walker carcinoma cells (Knox et al. (1988) *Biochem. Pharmacol*. 37:4661–4669) (see FIG. 1). The difference in sensitivity between rat and human cells (by a factor of $10^4$–$10^5$ in concentration) was shown to be the result of differences in the rates of reduction of CB1954 by rat and human DT diaphorases: the human form of DT diaphorase is intrinsically less able to reduce the compound than is the rat form (Boland et al., supra).

The 4-hydroxylamine toxic metabolite can be formed in one cell and can freely diffuse to produce cytotoxicity in another. This was demonstrated by co-culturing Walker cells and Chinese hamster V79 cells in the presence of CB1954. In the absence of the Walker cells, there was no killing of the V79 cells by CB1954, whereas in the presence of Walker cells, extensive killing of the V79 cells occurred (Knox et al. (1988) *Biochem. Pharmacol*. 37:4671–4677). We have shown that the toxic metabolite can diffuse through clostridial cell walls and, therefore, the toxic species can be formed within the nitroreductase-expressing recombinant.

This obviates the need for external NADH or NADPH co-factors, since *C. acetobutylicum* possesses both of these electron donors (Petitdemange et. al. (1976) *Biochem. Biophys. ACTA* 421:334–347). This is an advantage over the ADEPT approach, in which the enzyme is located outside of the cell requiring application of the co-factor. The nitroreductase enzyme is also found in the supernatant of recombinant *C. acetobutylicum*, showing that the enzyme is both within and outside the bacteria.

An enzyme particularly preferred for expression in recombinant *C. acetobutylicum*, is the nitroreductase enzyme from *E. coli* which was recently isolated and shown to reduce CB1954 at a rate 60 times greater than that of the rat DT diaphorase (Anlezark et al. (1992) *Biochem. Pharmacol*. 44:2289–2295). Similar to DT diaphorase, this *E. coli* nitroreductase also uses NADH and NADPH as co-factors, but unlike DT diaphorase, which reduces only the 4-nitro group of CB1954 to the hydroxyl amino species, the nitroreductase produces equal quantities of the 2 and 4 hydroxyl amino species (Knox et al. (1992) *Biochem. Pharmacol*. 44:2297–2301) (see FIG. 1). We have cloned and sequenced this enzyme.

(b) β-glucuronidase with Glucuronidated Anticancer Drugs

Glycosidase β-glucuronidase occurs in both prokaryotic and eukaryotic organisms. Its concentration in human serum is very low (Stahl et al. (1984) 1984:246–256), and, therefore, glucuronide prodrugs are relatively stable in blood following i.v. administration. Indeed, the conjugation of xenobiotics, including anticancer drugs, with glucuronide is a major route by which such drugs are eliminated (Connors et al. (1973) *Biochem. Pharmacol*. 22:1971–1980; Maftouh et al. (1984) *Drug Metab. Dispos*. 12:111–119; Weenen et al. (1984) *Eur. J. Cancer Clin. Oncol*. 20:1984). Since the glucuronide conjugation is extremely polar, the rate at which it enters cells would be expected to be much slower than that of the parent drug and hence less toxic.

Wang et al. ((1992) *Cancer Res*. 52:4484–4491) conjugated β-glucuronidase from *E. coli* to MAb RH1, a murine IgG that binds strongly to rat hepatoma cells, but not to human hepatoma cells. As a prodrug they tested a butylated ammonium salt of the glucuronide conjugate of hydroxyanaline mustard. They found that the prodrug was $10^3$ times less potent than hydroxyanaline mustard (HAM) and showed that when β-glucuronidase, either free or conjugated to the MAb, was added to the prodrug, it became as toxic as the nonglucuronide form, HAM. Similar results were obtained by Haisma and colleagues ((1992) *Br. J. Cancer* 66:474–478) who conjugated *E. coli*-derived β-glucuronidase to the anti-pan carcinoma, MAb 323/A3. As a prodrug, they used the glucuronide conjugate of epirubicin, an anticancer agent used in patients with breast cancer, lymphomas, ovarian cancer, and soft tissue sarcomas. They showed that the prodrug was approximately 100-fold less toxic to human breast and ovarian cancer cells, but became as toxic as epirubicin when combined with the MAb-β-glucuronidase conjugate.

c) Cytosine Deaminase and 5-fluorocytosine

Cytosine deaminase catalyzes the deamination of cytosine to uracil. Mammalian cells do not ordinarily produce this enzyme, whereas many bacteria and fungi do. Microorganisms that express cytosine deaminase can convert 5-fluorocytosine to 5-fluorouracil, a highly toxic metabolite that has potent cytotoxic effects on mammalian cells and is widely used as a cancer chemotherapeutic agent. (Mullen et al. (1992) *Proc. Natl. Acad. Sci. USA* 89:33–37) The bacterial gene for cytosine deaminase has recently been isolated and cloned.

EXAMPLES

Example 1

Preparation of Spores from *C. Acetobutylicum*

Conditions which induce sporulation in Clostridium spp are highly species- and strain-dependent. Since there are no published reports of methods to induce sporulation in strain NCIB 8052, a number of different media types and sporulation conditions were tried. Table 1 shows the different media and heat shock conditions used in the order in which they were attempted.

To check for the presence of the rodshaped, vegetative form of *C. acetobutylicum* in the tumors, the SCCVII tumors were sectioned along with several normal tissues from the same mice, sacrificed 24 hours after injection of the spores.

TABLE 1

*Clostridium acetobutylicum* sporulation

| Media | Media Changes | Heat Shock[a] | Incubator Temp (° C.) | % Sporulation | Suitability for i.v. injection |
|---|---|---|---|---|---|
| Brain Heart Infusion | — | — | 37 | <1 | |
| Brain Heart Infusion | — | 70° 10 min. | 37 | <1 | |
| CAMM(66) | — | — | 37 | <1 | |
| Chopped Meat | — | — | 37 | <1 | |
| Chopped Meat | — | 70° 10 min. | 37 | <1 | |
| Chopped Meat Carbohydrate | — | — | 37 | <1 | |
| Chopped Meat Carbohydrate | — | 70° 10 min. | 37 | <1 | |
| Chopped Meat Glucose | — | — | 37 | <1 | |
| Chopped Meat Glucose | — | 70° 10 min. | 37 | <1 | |
| Cooked Meat | — | — | 37 | <1 | |
| Peptone (4%) | — | — | 37 | <1 | |
| Peptone Yeast | — | — | 37 | <1 | |
| Peptone Yeast | — | 70° 10 min. | 37 | <1 | |
| Peptone Yeast Glucose | — | — | 37 | <1 | |
| Reinforced Clostridial | — | — | 37 | <1 | |
| Thioglycollate | — | — | 37 | <1 | |
| Thioglycollate | — | 70° 10 min. | 37 | <1 | |
| Starch(36) | — | — | 37 | 5–45 | poor |
| Starch(36) | — | 70° 5–40 min. | 37 | 1–6 | poor |
| Cooked Meat | pellets removed | — | 37 | 10–65 | good |
| Cooked Meat | no pellets/ +2% peptone | — | 37 | 10–65 | good |
| Cooked Meat | pellets removed | — | 25 | 20–65 | good |
| Cooked Meat | pellets removed | — | 30 | 30–85 | good |

[a]Heat shock of exponential culture just prior to addition to sporulation media.

A cooked meat medium (Difco Laboratories, Detroit) is employed and is suitable for animal injection as it is entirely in solution and is easily removed with several PBS washes. This medium is prepared according to the manufacturer's instructions, except that the media pellets are removed for sporulation, as this greatly enhances the spore yield, presumably by making the media less rich.

Example 2

Oncolysis of Tumors by *C. Acetobutylicum*

Figure 2A:
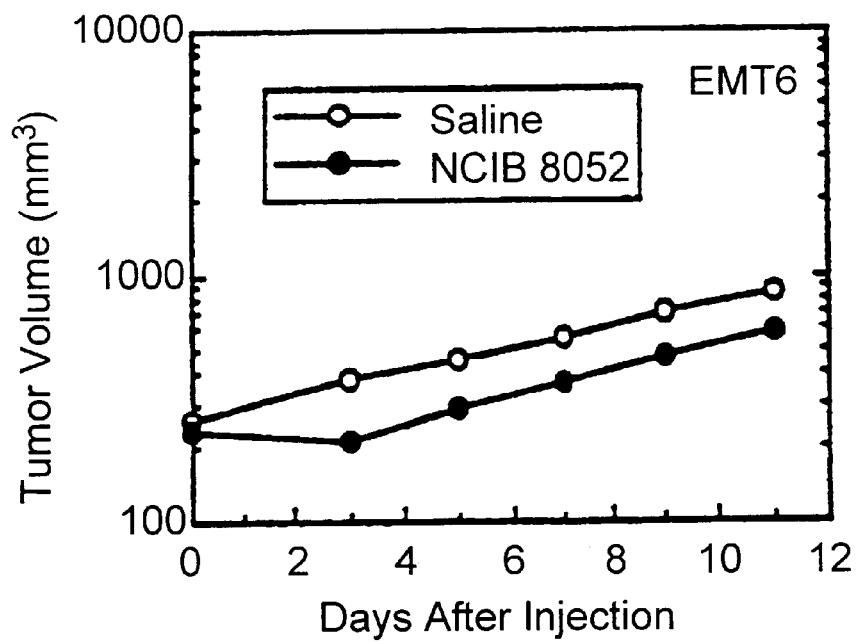
FIGS. 2A–2B show tumor volumes of intradermally implanted EMT6 and SCCVII tumors as a function of time after intravenous injection of $10^8$ spores of *C. acetobutylicum*. The data show group means (5 mice per group). The standard errors of the means are smaller than the points plotted.
Figure 2B:
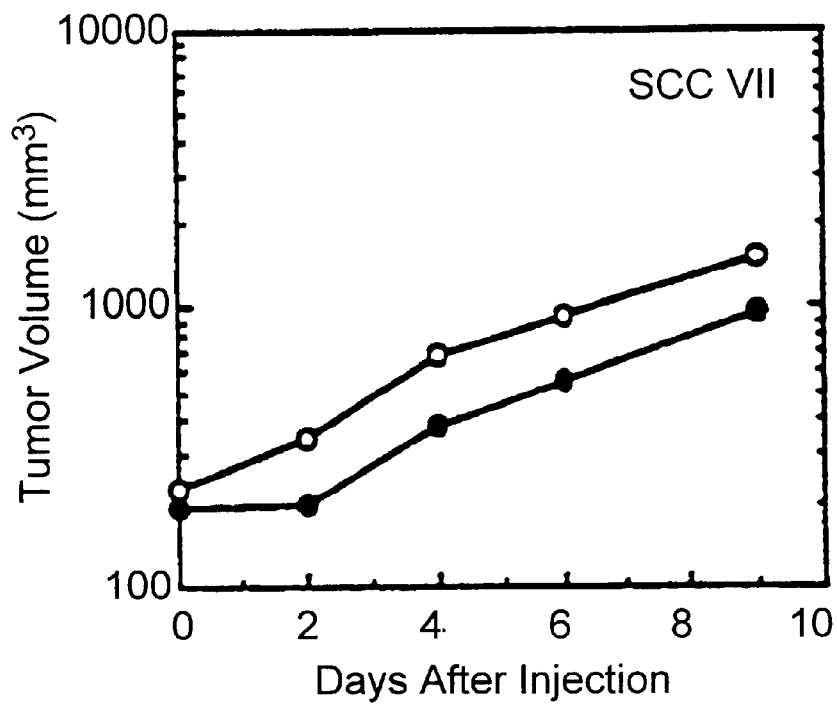
Figure 3A:
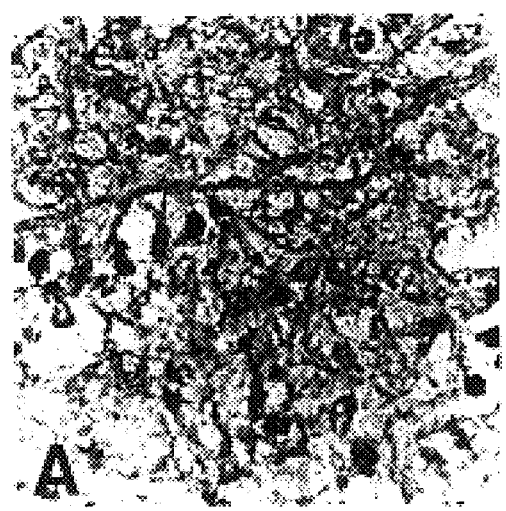
FIG. 3A shows the necrotic region from a saline injected mouse.
Figure 3B:
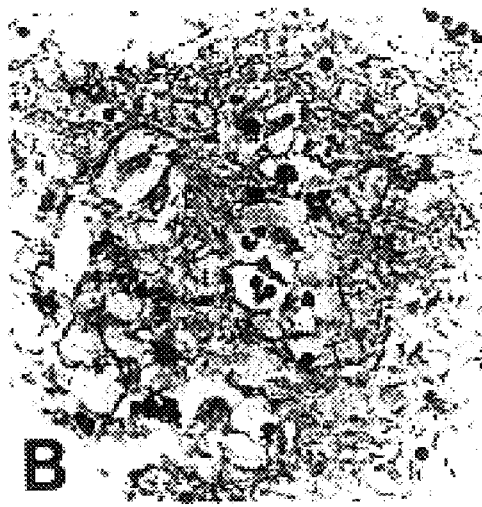
FIG. 3B shows the necrotic region from a *C. acetobutylicum* injected mouse 24 hours after spore injection with many gram positive rods visible.
Figure 3C:
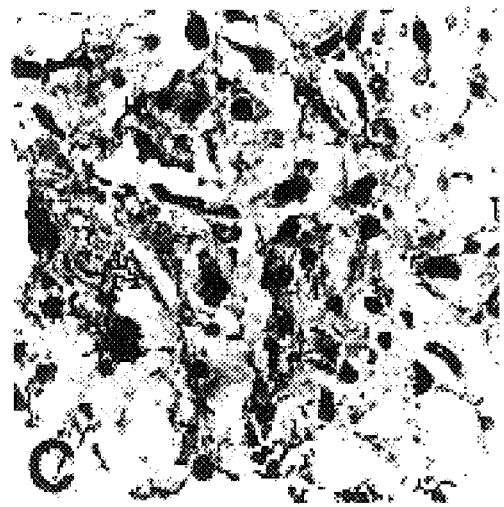
FIG. 3C shows the border between necrotic and non-necrotic regions from a *C. acetobutylicum* injected mouse 24 hours after spore injection.
Figure 3D:
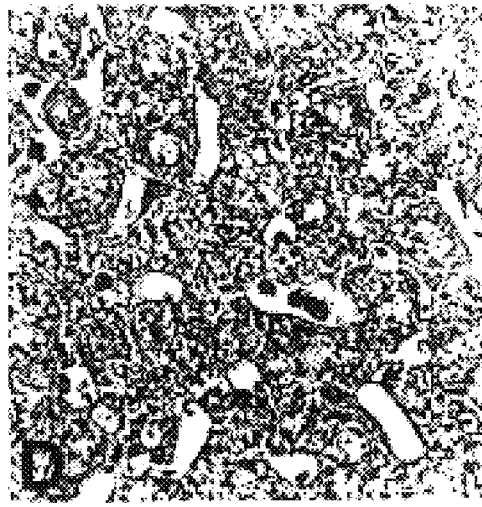
FIG. 3D shows a liver section stained with Gram-Twort from the same mouse as in B and C with no evidence of bacteria.

In order to test the ability of spores of *C. acetobutylicum* to germinate and produce tumor lysis, mice bearing either EMT6 or SCCVII tumors were injected intravenously with 0.1 ml saline, or the same volume of saline containing $10^8$ spores of *C. acetobutylicum* NCIB 8052. Prior to injection, the spores were heat shocked at 80° C. for 20 min to activate them to return to the vegetative form and to kill the vegetative rods, which are always present in the sporulation cultures. Following injection, the tumor volumes were determined three times weekly from the product of three mutually perpendicular diameters. FIGS. 2A–2B shows the results of this experiment. In the tumors injected with the clostridial spores, there was a slight shrinkage or delay in growth of the tumors for two to three days, after which they grew at the same rate as control tumors. Partial tumor lysis was observed in all of the EMT6 tumors. In this experiment, no obvious tumor lysis was seen in the SCCVII tumors, though in early experiments with larger SCCVII tumors, this was observed.

Examples of photomicrographs taken on these tumors and from normal liver are shown in FIG. 3.

Typically, the rod-shaped, vegetative form of *C. acetobutylicum* was observed in necrotic areas of the tumor, with some invasion into surrounding viable-looking tumor tissue. There was no evidence of remaining spores in these sections. Overall, it appears that the maximum number of metabolizing clostridia, and hence the maximum production of nitroreductase, depends on the extent of hypoxia and/or necrosis in the tumor.

Example 3

Expression of the *E. Coli* ntr Gene in *C. Acetobutylicum*

(a) General Considerations

The gene (ntr) encoding *E. coli* B nitroreductase (NTR) was cloned and its entire nucleotide sequence determined. The fragment characterized was shown to carry the ntr promoter in addition to the structural gene. The transcriptional initiation signals of a Gram-negative bacterium are extremely inefficiently utilized by Gram-positive bacteria. In addition, Gram-negative ribosome binding sites (RBS) are poorly recognized by Gram-positive ribosomes. mRNA transcripts would not be translated into product. In order to successfully express a Gram-negative gene in Clostridium spp., it was necessary to replace both the Gram-negative promoter and RBS with Gram-positive equivalents.

Based on the previously constructed *E. coli* Clostridium cloning vector, pMTL500E (Oultram et al. (1988) *FEMS*

Figure 10:
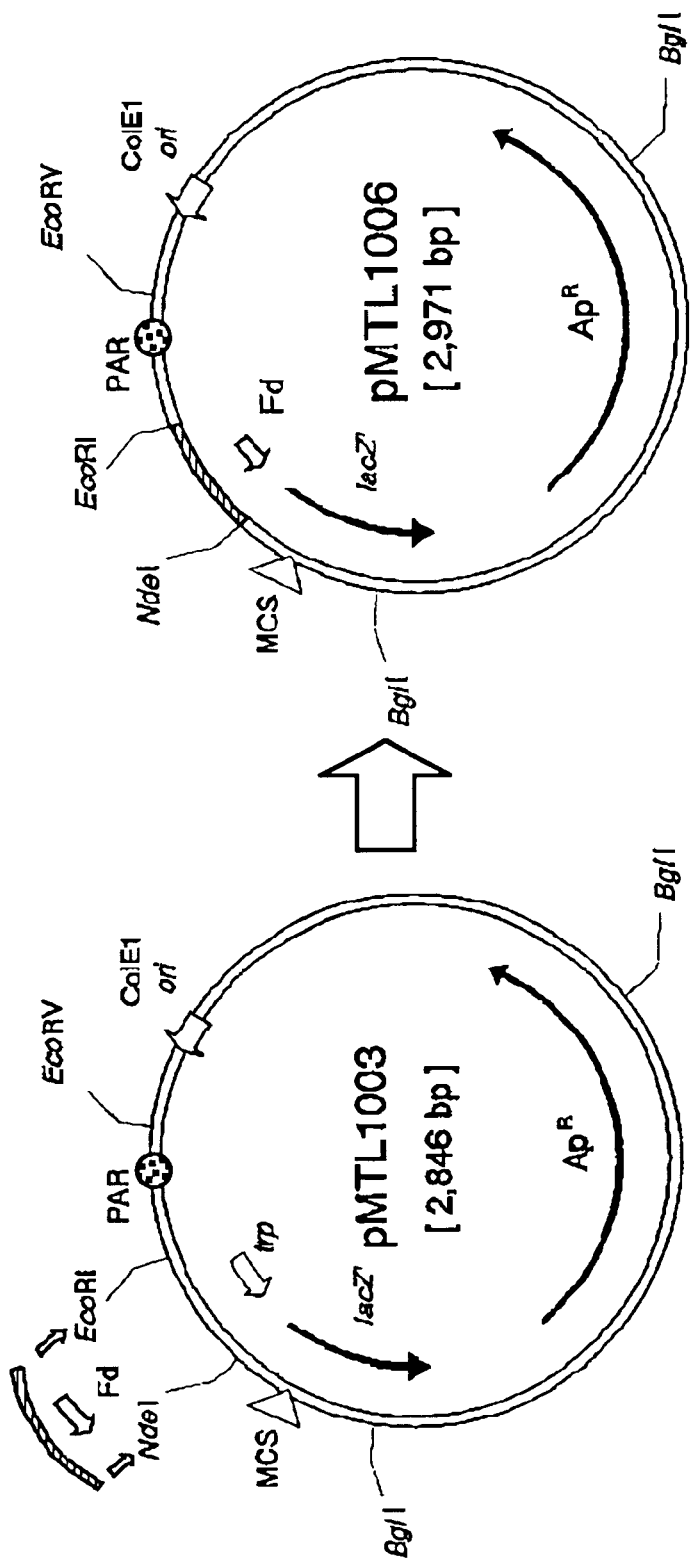
FIG. 10 illustrates the construction of pMTL1006. Plasmid pMTL1006 was derived from pMTL1003 by replacing the trp promoter of the latter with the modified Fd promoter shown in FIG. 10. The MCS is that of pMTL20 (Chambers et al. (1988) *Gene* 68:139–149). Key: MCS=multiple cloning site; Ap=ampicillin; $^R$=resistance; PAR=the partition locus of plasmid pSC101; trp=the *E. coli* trpE promoter; ori=origin of replication; and Fd=ferredoxin gene promoter.
Figure 11:
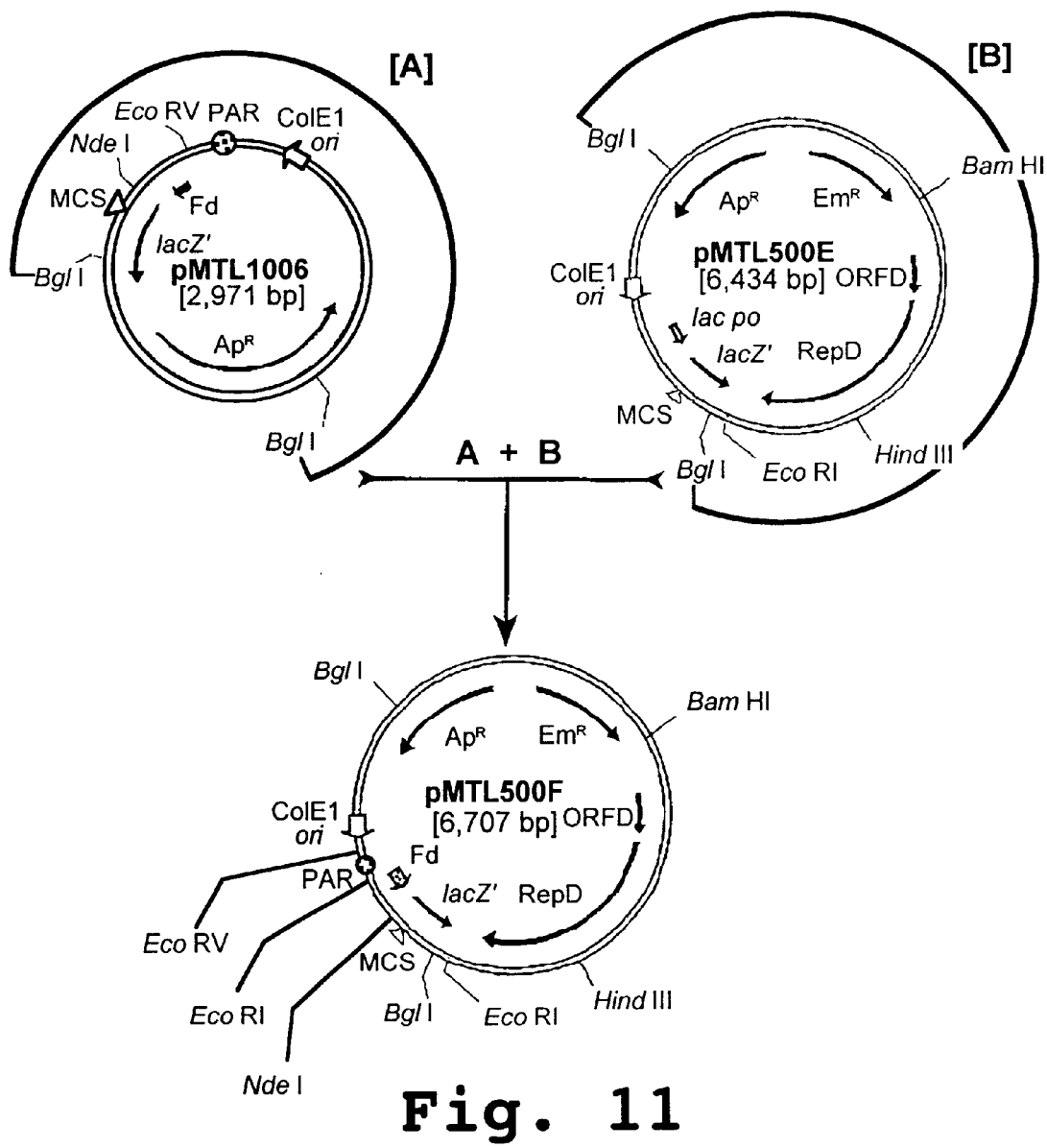
FIG. 11 illustrates the construction of the expression vector pMTL500F. Following cleavage of pMTL1006 and pMTL500E with BglI, the indicated fragments (A and B) were isolated from the respective plasmids and ligated together to give plasmid pMTL500F. Key: Em=erythromycin; lac po=the promoter/operator region of the *E. coli* lac operon.
Figure 12:
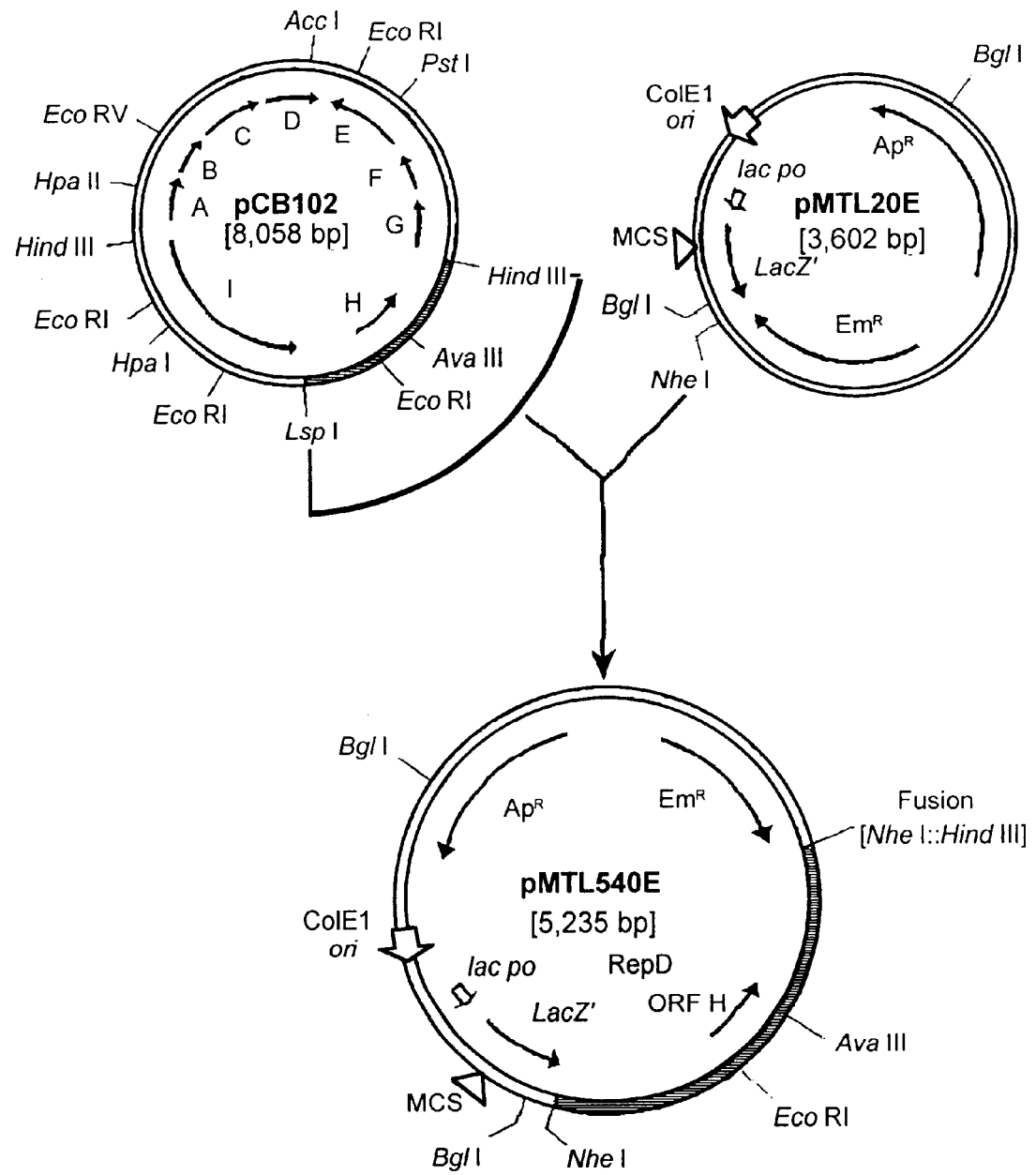
FIG. 12 illustrates the construction of the cloning vector pMTL540E. Plasmid pCB102 was digested with HindIII and LspI, the fragments generated blunt-ended by treatment with T4 DNA polymerase and a 1.53 Kb fragment carrying the pCB102 minimal replicon region isolated. The replicon probe vector pMTL20E was digested with NheI, blunt-ended with T4 DNA polymerase, and ligated to the isolated LspI-HindIII fragment. The resultant plasmid was designated pMTL540E. The arrows within the map of pCB102 correspond to the major open reading frames (ORFs) identified following translation of its nucleotide sequence. Only ORF H may play some role in replication.

*Microbiol. Letts.* 56:83–88) the promoter and RBS of the lacZ' were replaced in pMTL500F by the equivalent signals of the ferredoxin (Fd) gene of *Clostridium pasteurianum* (see FIG. 4). A 604 bp MboI fragment carrying the *Clostridium pasteurianum* ferredoxin gene was isolated from the genome of strain ATCC 6013 and cloned into the BamHI site of M13mp7. The nucleotide sequence of the cloned fragment was found to be identical to that reported by Graves et al. (1985) *Proc. Natl. Acad. Sci. USA* 82:1653–1657. Site-directed mutagenesis (SDM) was used to change the triplet immediately preceding the translational start codon from TTC to CAT, thereby creating a recognition sequence for the restriction enzyme NdeI. A unique HpaI site was also created within the promoter region by changing nucleotide position 132 (Graves et al. (1985) *Proc. Natl. Acad. Sci. USA* 82:1653–1657) from "A" to "T." Into this created site a 25 bp blunt-ended, synthetic DNA fragment corresponding to the operator of the *E. coli* lac promoter. The modified Fd promoter was subsequently isolated as a 200 bp fragment (see FIG. 9), following cleavage with NdeI and EcoRI, and cloned between the equivalent sites of the expression vector pMTL1003 (Brehm et al. (1991) *Appl. Microbiol. Biotechnol.* 36:358–363) to give pMTL1006 (see FIG. 10). The final step involved replacing the lac promoter of pMTL500E with the Fd promoter of pMTL1066. This was achieved by combining a 1.871 Kb BglI fragment isolated from pMTL1006 with a 4.839 Kb BglI fragment isolated from pMTL500E (see FIG. 12). The resultant plasmid was designated pMTL500F.

(b) Construction of the Vectors and Expression of Nitroreductase

Figure 4:
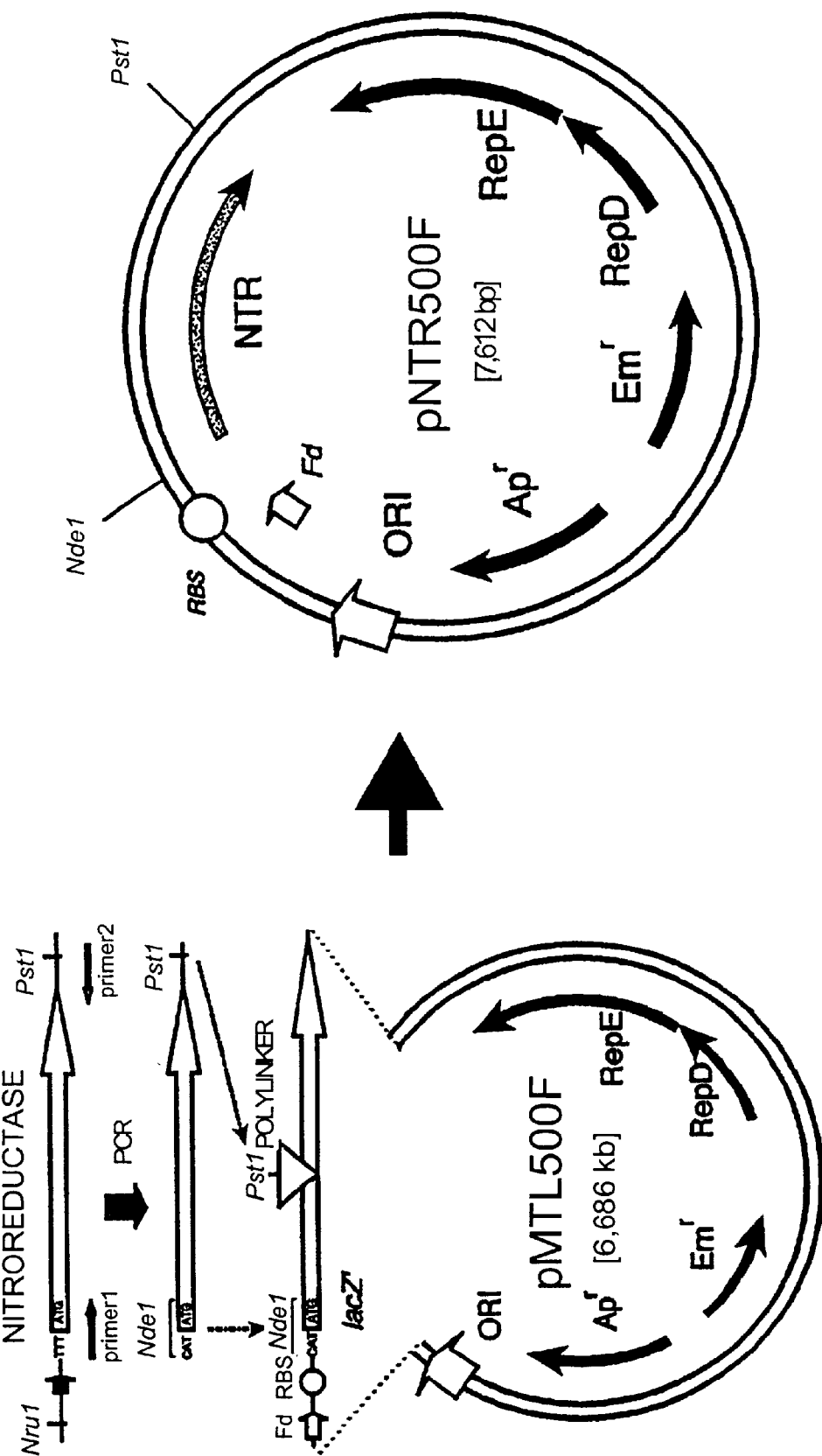
FIG. 4 illustrates the construction of a clostridial vector (pNTR500F) expressing nitroreductase.

Capitalizing on the specialized features of pMTL500F, a recombinant plasmid capable of directing the expression of the ntr gene in *C. acetobutylicum* was derived as illustrated in FIG. 4. In essence, a Nde1 site was created 'over' the translational start codon of the ntr gene allowing its subsequent insertion into pMTL500F immediately adjacent to the clostridial Fd promoter and RBS. Two oligonucleotide primers were employed to amplify a 700 bp fragment carrying the *E. coli* B nitroreductase gene. Simultaneously, primer 1 created an Nde1 site. The amplified fragment was subsequently inserted between the Nde1 and Pst1 sites of the expression vector pMTL500F. In the resultant recombinant, pNTR500F, the ntr gene is under the transcriptional and translational control of the promoter (Fd) and ribosome binding site (RBS), respectively, of the *C. pasteurianum* ferredoxin gene. Ap' and Em'-and ampicillin are erythromycin resistance genes, respectively. RepD and RepE are pAMβ1-derived replication proteins, and ORI is the replication origin of ColE1.

Following its construction in *E. coli*, pNTR500F was transformed into *B. subtilis* and *C. acetobutylicum* NCIMB 8052, and lysates prepared from overnight cultures of all three hosts harboring either pMTL500F or pNTR500F. All three lysates derived from cells carrying pNTR500F contained an abundant polypeptide species of around 24 kDa, not evident in the control lysates derived from cells harboring the vector alone. Western blots using appropriate anti-NTR antibodies demonstrated that this protein corresponds to the *E. coli* NTR. A less abundant protein of equivalent size present in lysates derived from cells carrying pMTL500F was negative by the same test. Densitometric scanning of electrophoretograms indicated that the level of NTR produced by *C. acetobutylicum* was 8% of the cells' soluble protein.

(c) Improved Clostridial Expression Vectors

Figure 13:
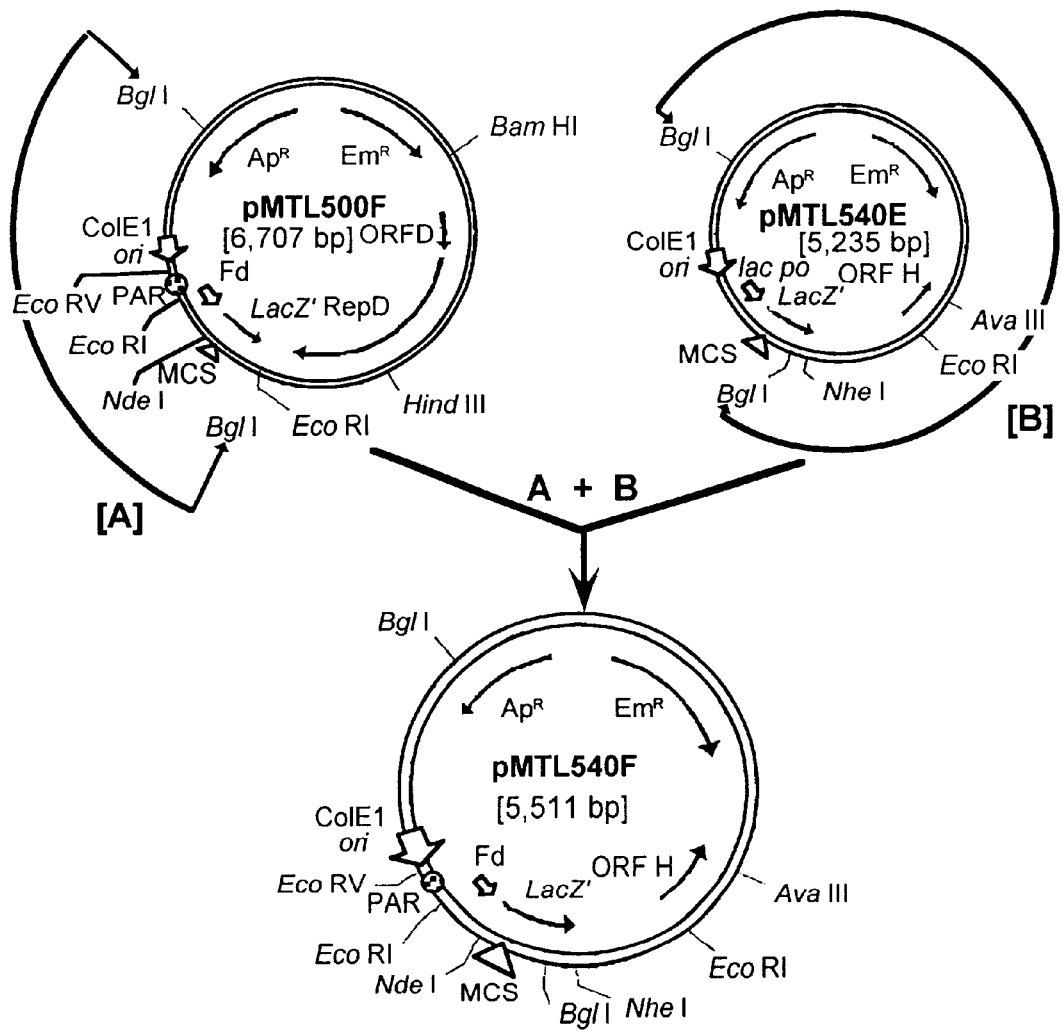
FIG. 13 illustrates the construction of the expression vector pMTL540F. Following cleavage of pMTL500F and pMTL540E with BglI, the indicated fragments (A and B) were isolated from the respective plasmids and ligated together to give plasmid pMTL540F.

A new version of pMTL500F has been constructed, designated pMTL540F, in which the pAMB1-derived replication origin was replaced with a replicon derived from the *Clostridium butyricum* plasmid pCB102 (Minton, N. P. and J. G. Morris (1981) *J. Gen. Microbiol.* 127:325–331). Plasmid pMTL540F was constructed in an analogous fashion to pMTL500F. First, a similar plasmid to PMTL500E was made, pMTL540E (see FIG. 12), by inserting a blunt-ended 1.53 Kb LspI-HindIII fragments from pCB102 into the NheI site, similarly blunt-ended, of the replicon cloning vector pMTL20E (Swinfield et al. (1990) *Gene* 87:79–89). The lac promoter of pMTL540E was then replaced with the promoter of the Fd gene by combining a 3.64 Kb BglI fragment from pMTL540E with a 1.871 Kb BglI fragment isolated from pMTL500F (see FIG. 13). The resultant plasmid was designated pMTL540F. Plasmids pMTL540E and pMTL540F exhibit a greater degree of segregational stability in *Clostridium acetobutylicum* compared to pMTL500E and pMTL500F.

Example 4

Detection of Nitroreductase in Vitro and in Vivo

Most sensitive biochemical assays for NTR activity utilize the quinone reductase properties of the enzyme and employ substrates (dichlorophenol-indophenol and cytochrome c) which work equally well as electron donors for both mammalian and bacterial enzymes. The broad substrate specificity of NTR and the presence of other enzymes (e.g., quinone of oxidoreductase, aldehyde oxidase) which catalyze similar reactions make the assay of a specific enzyme within a crude cell homogenate problematic. Several methods were developed to unequivocally detect recombinant NTR expression in bacterial cultures and tumor tissue.

(i) Nitroreductase Activity in Vitro

To quantify expression of the recombinant *E. coli* NTR in bacterial cultures, a spectrophotometric enzyme activity assay was used to measure NTR activity in the supernatant and cell pellet fractions of transformed clostridial cultures. This assay, based upon the reduction of dichlorophenol-indophenol in the presence of NADH, demonstrated that clostridia transformed with the plasmid containing the *E. coli* ntr gene (pNTR500F) exhibit a 200-fold increase in NTR activity when compared to the endogenous activity of the parental wild-type strain in mid-log phase cultures (44 U/mg protein in culture supernatants for transformed *C. acetobutylicum* vs 0.2 U/mg for the parental strain). In early log phase cultures, total NTR activity was low (4 U/mg protein) and greater than 95% of the enzymatic activity was associated with the cell pellet. As cultures progressed into stationary phase, NTR activity accumulated within the culture media and was increasingly found in the supernatant fraction. By 24 hrs post-inoculation, total NTR activity within the culture had risen to 105 U/mg protein, and 95% of the activity was associated with the supernatant fraction of the culture.

*E. coli* NTR activity was visualized in nondenaturing polyacrylamide gels. FIG. 5A demonstrates the ability to detect recombinant NTR in mixtures of lysates from *C. acetobutylicum* and EMT6 tumor cells. Lysates from NTR-transformed *C. acetobutylicum* and EMT6 tumors were mixed together, run on a native gel, and stained for NTR activity. Although both bacterial NTR and mammalian DT diaphorase were detected by this technique, the different electrophoretic mobilities of the two enzymes allowed NTR activity from as little as 250 ng *C. acetobutylicum* lysate to be easily visualized in the presence of a 200-fold excess of EMT6 protein.

Western blotting was also used to detect recombinant NTR in tumor lysates. FIG. 5B shows a blot, stained with anti-*E. coli* NTR antibody, containing EMT6 tumor samples removed four days following i.v. injection of saline, wild type *C. acetobutylicum* spores, or spores from NTR-transformed bacteria into tumor bearing mice. The antibody detects protein of approximately the appropriate size (27 kD) and mobility of the NTR protein standard in the two samples derived from tumors injected with spores expressing recombinant NTR. NTR protein is not detectable in tumor samples derived from animals injected with saline or wildtype *C. acetobutylicum*. An additional protein (77 kD) was also detected by this antibody in all tumor samples. This blot demonstrates that *C. acetobutylicum* spores are vectors capable of expressing recombinant proteins in vivo and that these recombinant proteins can be detected in tumor homogenates.

Figure 6:
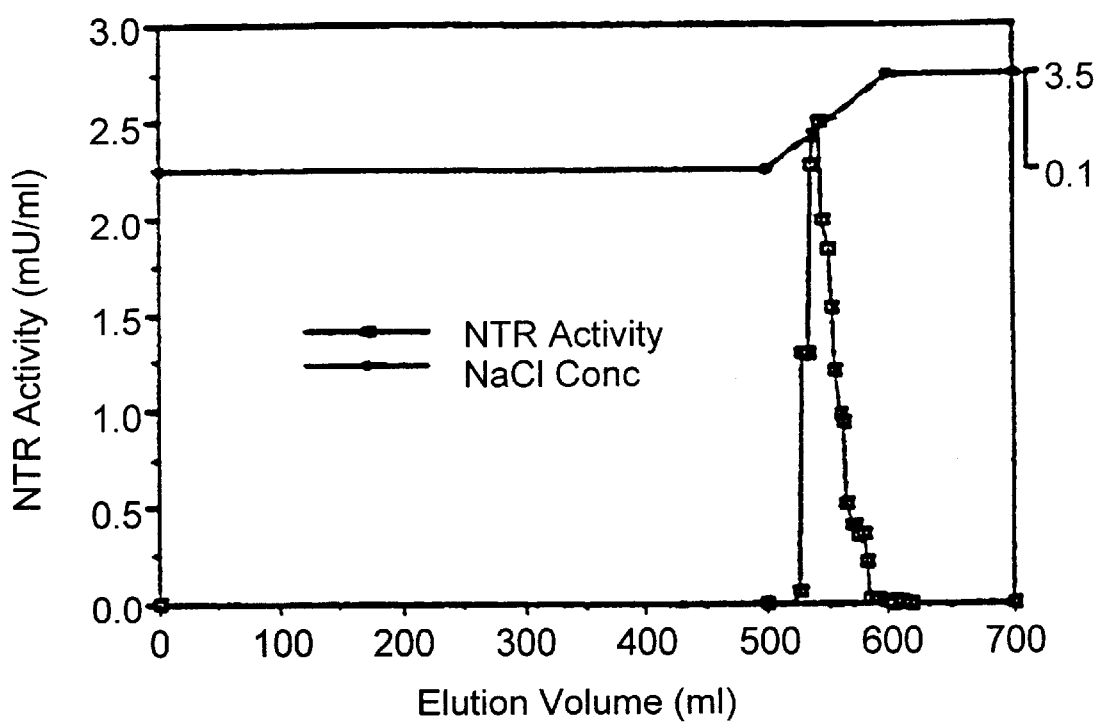
FIG. 6 shows an elution profile from dye affinity chromatography purification of NTR from *C. acetobutylicum*.

Recombinant *E. coli* nitroreductase was partially purified from transformed *C. acetobutylicum* using a modification of the affinity chromatography technique of Ysern and Prochaska ((1989) *J. Biol. Chem.* 264:7765–7767). A preliminary isolation yielded a 100-fold purification of nitroreductase in a single affinity chromatography step from a clarified homogenate of *E. coli* expressing the nitroreductase plasmid. The homogenate was passed over a dye affinity column (Affi-Gel Blue, Bio-Rad) and washed with increasing concentrations of NaCl. A highly enriched nitroreductase fraction was eluted from the column in a 1 M NaCl wash (FIG. 6). Denaturing polyacrylamide gel electrophoresis of the eluted fraction followed by silver staining demonstrated at least four strongly staining protein bands. The major constituent was estimated to have a molecular weight of 26.5 kDa, very close to the reported size of 24 kDa for *E. coli* nitroreductase (Anlezark et al., (1992) *Biochem. Pharmacol.* 44:2289–2295). Further purification steps produced a preparation of sufficient purity to use as antigen for antibody production and standards in the ELISA assay, native gel electrophoresis, and immunoblotting assays.

In order to test the ability of recombinant *C. acetobutylicum* to activate CB1954, recombinant and wild type *C. acetobutylicum* were inoculated into 20 ml of medium. After overnight incubation, the cultures were centrifuged and the supernatant collected and diluted 1:3 with Waymouth's growth medium. This mixture, which had a pH of approximately 6.9, was then transferred to 60 mm plastic petri dishes containing SCCVII tumor cells, which were approximately 50% confluent. To these cultures, different concentrations of CB1954 in DMSO were added, and the amount of DMSO adjusted in all of the cultures (including the controls) to 1% DMSO. Controls consisted of cell culture with only the supernatant/cell culture medium mixture. All plates received NADH to a final concentration of 500 $\mu$M.

Figure 7:
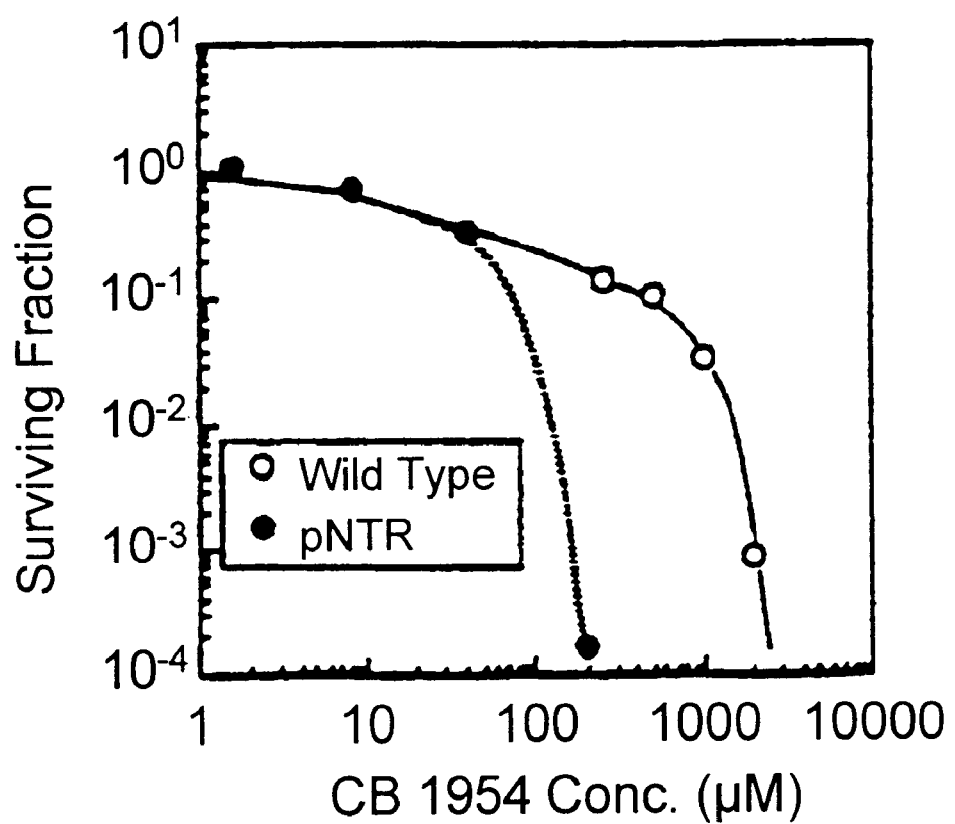
FIG. 7 illustrates cell killing of SCCVII cells in vitro exposed to CB1954, NADH (500 μM), and supernatants from wild type or recombinant *C. acetobutylicum*.
Figure 8A:
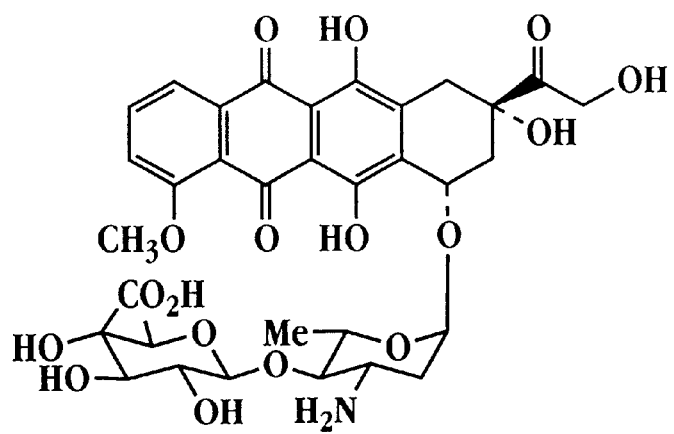
FIGS. 8–8B show structures of the glucuronides of the three primary synthetic targets epirubin, 5-fluorouracil, and 4-hydroxycyclophosphamide.
Figure 8B:
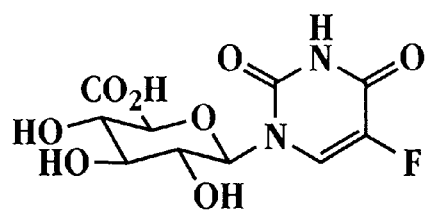
Figure 8C:
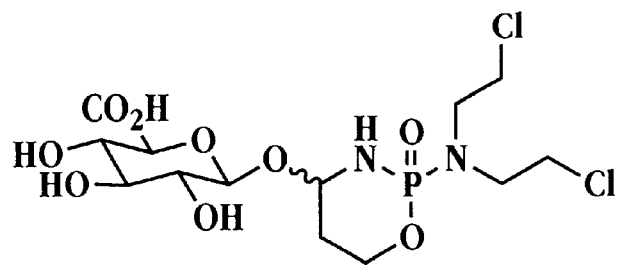

After a 2 hr incubation in air at 37° C., the medium was removed, all the plates were washed 3 times with PBS, trypsinized, the cells counted by hemocytometer, and appropriate dilutions plated and incubated for 10 days in a 5% $CO_2$ incubator at 37° C. for colony growth. The results are shown in FIG. 7.

The results show that the supernatant from the transformed *C. acetobutylicum* is capable of enhancing the toxicity of CB1954 by a factor of approximately 10 in concentration.

(ii) Nitroreductase Activity in Vivo

In vivo studies with three different transplanted mouse tumors, EMT6, SCCVII and RIF1 tumors and with human colon carcinoma HT29 transplanted into immune-deficient SCID mice were performed. Tumors were injected with spores of control and recombinant *C. acetobutylicum* when the subcutaneous tumors reach a diameter of between approximately 0.5 and 1 cm. As a function of time after injection, mice are sacrificed and their tumors removed.

First, homogenates of the tumors were prepared, extracts run on a nondenaturing gel and then the amount of nitroreductase was quantitated with a Western blot. See FIG. 5B. Homogenates of normal tissue show no detectable levels of nitroreductase protein.

Second, in order to see the intertumor localization of the protein, certain tumors were immediately fixed in formaldehyde and sectioned, the NTR antibody applied and detected with a second antibody linked to horseradish peroxidase. This immunohistochemistry detected the location of extracellular nitroreductase in tumor specimens. ELISA assays are also employed to quantitate the amount of nitroreductase in the tumor.

(iii) In Vivo Efficacy Studies

Prodrugs such as CB1954, glucuronides of epirubin, 5-fluorouracil and 4-hydroxycyclophosphamide, and 5-fluorocytosine, are injected into mice at different times during the growth of the *C. acetobutylicum* in the tumors and the response of the tumor, as measured both by clonogenic cell survival and by growth delay, to both nitroreductase expression and to metabolism of CB1954 is determined.

The extent of tumor cell destruction at nontoxic doses for the clostridia+prodrug invention is compared to the results achieved by systemic administration of the active metabolite of the prodrugs. The active metabolites of the prodrugs are synthesized using standard methodology and injected intravenously at nontoxic doses. Tumor response is measured by total clonogenic cells per tumor assayed 24 hrs after treatment and by regrowth delay. Efficacy of treatment is indicated by greater tumor response with the clostridial targeting vector+prodrug than achievable with active metabolite achieved systemically.

(iv) Influence of Level of Hypoxia/Necrosis

To determine the relative dependency of the growth of the recombinant clostridia and resultant production of the nitroreductase enzyme on the extent of necrosis and/or hypoxia in a tumor, two tumors, the SCCVII and RIF-1 transplantable mouse tumors, are employed which allow for alteration of the extent of hypoxia and necrosis in reproducible ways. The in vivo studies described above of the expression of nitroreductase, metabolism of CB1954, and in vivo efficacy in tumors are performed with levels of hypoxia and necrosis increased in two different ways.

First, tumor hypoxia/necrosis is increased by implanting the above two tumors in a previously irradiated normal tissue. Several authors have shown that tumors growing in irradiated normal tissues have a higher hypoxic fraction and more necrosis than the same tumors growing in unirradiated tissue (Malmgren et al. (1955) *Cancer Res.* 15:473; Penhaligon et al. (1987) *Int. J. Radiat. Biol.* 52:635–641). In similar studies using the SCCVII and RIF-1 tumors, both a decrease in tumor $pO_2$ measured using the Eppendorf polarographic electrode and an increase in $^3$H-MISO binding in tumors transplanted either into the thigh muscle or subcutaneously in the back was observed if these normal tissues had been irradiated up to four months earlier with a dose of 20 Gy (Kim et al. (1993) *Rad. Res.* 135:411–417). In these experiments, the radiobiological hypoxic fraction was also increased. This system is employed and monitored using the Eppendorf electrode (which measures both viable hypoxic cells and necrosis) and $^3$H-MISO binding (which measures hypoxia only in viable tissue) to determine the influence of different levels of hypoxia and necrosis on the response of tumors to recombinant C. acetobutylicum with CB1954.

Secondly, the influence of different levels of hypoxia and necrosis for these two tumors is determined using the anticancer drug, flavone acetic acid (FAA, NSC 347512). This drug, which has been tested clinically both in Europe and in the U.S., has so far not proved effective in human tumors (Kerr et al. (1989) Br. J. Cancer 60:104–106). However, it has been shown by a number of investigators (Sun, J. R. and J. M. Brown (1989) Cancer Res. 49:5664–5670) that this drug causes a profound and prolonged decrease in tumor blood flow and the formation of hemorrhagic necrosis within the tumors. The necrosis, which is observed within one day, is focal and can be extensive. C. acetobutylicum spores are injected one day subsequent to injecting FAA when there is a large increase in tumor necrosis. In both studies comparing the results of control tumors with tumors in which the hypoxia or necrosis has been increased, the response of the SCCVII and RIF-1 tumors is assayed using cell survival and growth delay as the endpoints.

Example 5

Expression of the β-glucuronidase Gene (uidA) in C. Acetobutylicum

Oligonucleotide primers, based on the published sequence (Jefferson et al. (1986). Proc. Natl. Acad. Sci. USA 83:8447–8451), are utilized to amplify a fragment carrying uidA from E. coli K12, and thereafter appropriate primers are used to authenticate its entire nucleotide sequence. As with the ntr gene, one of the PCR primers employed creates an Nde1 site 'over' the uidA start codon, to facilitate insertion of the gene into pMTL500F. The resultant plasmid is then transformed into C. acetobutylicum NCIMB 8052, and expression studies conducted.

Unlike NTR, where access to bacterial cytoplasmic co-factors is adventitious, for activity the β-glucuronidase has to be exported out of the clostridial cell. To achieve this, the uidA gene is endowed with a 5' signal sequence to promote secretion of the translated protein by the classical signal peptide route (Bosslet et al. (1992) Br. J. Cancer 65:234–238). Two signal sequences are employed: (1) the Clostridium thermocellum celA gene (Beguin et al. (1985) J. Bacteriol. 162:102–105); and (2) the staphylococcal protein A gene (Shuttleworth et al. (1987) Gene 58:283–295). The 5'-end of the lacZ' gene of pMTL500F (that residing between the Nde1 site and polylinker region, see FIG. 4) is replaced with DNA specifying the two signal sequences, approximately 10 or so codons past the signal peptidase encoded cleavage site. Thereafter, a suitably modified copy of the uidA gene (one in which a restriction site is introduced by site-directed mutagenesis at the second codon) is introduced into the polylinker region of the two resultant plasmids, such that in phase fusion occurs between the celA- or spa-derived sequences. The efficiency with which the resultant CelA::UidA and Spa::UidA fusion proteins are exported from C. acetobutylicum cells is assessed. Maximum efficiency of secretion and enzymic activity of the processed fusion protein, may require some experimentation in the number of celA/spa-derived amino acids at the NH2-terminus of the created fusion proteins.

Example 6

Recombinant Stability

The integrity of the enzyme-encoding genes introduced into C. acetobutylicum are stably maintained during bacterial cell multiplication within the tumor, and these genes are partitioned with high fidelity to each successive daughter cell in the absence of selective pressure, i.e., antibiotic resistance. Unlike B. subtilis, structural instability has not proven problematical in C. acetobutylicum. Plasmid pMTL500F, like its progenitor pMTL500E, is, however, segregationailly unstable. Thus, when C. acetobutylicum cells carrying pMTL500E or pMTL500F are grown in erythromycin-free media, the probability of plasmid loss at cell division is $4 \times 10^{-2}$, e.g., after 20 generations over 50% of the cells will have lost the plasmid. This form of instability is a general characteristic of all currently available vectors (Minton et al. (1993) "Clostridial cloning vectors," In: THE CLOSTRIDIA AND BIOTECHNOLOGY (Woods, D. R., eds. Butterworth-Heinemann Publishing).

(a) Stabilization of Autonomous Elements

Currently available C. acetobutylicum vectors are based on a very limited number of plasmids, namely the Clostridium butyricum plasmid pCB101, the B. subtilis plasmid pIM13, and the enterococcal plasmid pAMβ1 (65, 71). The segregational stability of vectors based on two other C. butyricum plasmids, pCB103 and pCB102 is determined (Minton et al. (1981) J. Gen. Microbiol. 127:325–331), the latter of which has been completely sequenced. The plasmid pAMβ1 has been previously shown to carry a resolvase gene (res) which stabilizes plasmids by maintaining the plasmid population in the monomeric state (Swinfield et al. (1990) Gene 87:79–90). When inserted into the polylinker region of pMTL500E, to give pMTL500res, a 10-fold improvement in segregational stability was obtained by reducing the probability of plasmid loss at each generation to $4 \times 10^{-3}$, i.e., after 20 generations in the absence of antibiotic selection, 90% of the cells still retain the plasmid. In view of these results, the res gene is incorporated into pMTL500F. In pAMβ1 the res gene is located immediately adjacent to the origin of replication. In plasmid pMTL500Eres, these two elements became physically separated by vector DNA. In pMTL500F, res is positioned precisely adjacent to the pAMβ1 origin. By analogy to other studies in B. subtilis, this could result in effectively 100% segregationally stable vectors (Janniere et al. (1990) Gene 86:53–61).

(b) Integration of Heterologous Genes

One of the most effective mechanisms for ensuring that recombinant genes are stably maintained is to bring about their incorporation into the host chromosome. Although integrative procedures are commonplace in other genera, there are no published examples in Clostridium spp. Recently, it has been demonstrated that integration can be achieved in C. acetobutylicum. In this study a central portion of the C. acetobutylicum gutD gene (encoding glucitol dehydrogenase) was inserted into a erm+version of the replication impaired plasmid pMTL20CB13 (Swinfield et al.

(1990) *Gene* 87:79–90). After 50 generations of growth in antibiotic-free medium, 99.99% of cells were no longer resistant. Furthermore, the plasmid was shown to have integrated into the chromosome by a Campbell-like mechanism in all 15 randomly chosen erythromycin-resistant colonies. The ntr and β-glucuronidase (uidA) genes are integrated by double crossover. This involves creating a plasmid which carries the 5' and 3' ends of the gutD gene, but in which the central portion of gutD is replaced by ntr or uidA and a selectable marker. In the initial experiments this marker is the erm gene. To bring about integration, the pMTL20CB13 derivative carrying the gutD'::ntr::erm::'gutD "cassette" is transformed into *C. acetobutylicum* and cells grown for 50 generations in antibiotic-free media, whereupon they are plated on agar media containing erythromycin. The DNA of erythromycin-resistant colonies subsequently shown to be unable to grow on sorbitol as a sole carbon source is then used in a PCR with primers based on sequences from the 5' and 3' end of gutD. The generation of a DNA fragment of an increased size consistent with the additive length of ntr::erm confirms that such cells are integrants. The enhanced stability of such integrants is assessed by prolonged growth in the absence of antibiotic.

In order to produce a recombinant microorganism with less potential risk, the erm gene is replaced by a more innocuous selective marker. It has been demonstrated that a cloned leuB gene from *C. pasteurianum* can complement the leucine deficiency of a mutant derivative of *C. acetobutylicum* when the gene is introduced either cloned in pMTL500E (Oultram et al. (1988) *FEMS Microbiol. Letts.* 56:83–88) as part of large co-integrate plasmid (Oultram et al. (1988) *Mol. Gen. Genet.* 214:177). A gutD'::ntr::leuB::'gutD cassette is assembled and cloned into a pMTL20CB13 derivative which also carries erm. Cells carrying such a plasmid are grown for 50 generations in a rich media and plated on glucose minimal media lacking leucine. Cells containing the autonomous plasmid retain erythromycin resistance and are able to utilize sorbitol as a carbon source. Those cells in which integration has occurred are unable to grow on sorbitol-minimal and exhibit sensitivity to erythromycin. Clones of this latter type are characterized by Southern blot and diagnostic PCR analysis and thereafter are subjected to stability studies.

Example 7

Optimization of Heterologous Expression

Although the protein levels obtained using Fd are reasonably respectable, far higher expression levels are achieved in other bacterial systems. The methods to increase expression levels of both the nitroreductase and β-glucuronidase enzymes are outlined below.

(a) Comparative Studies using Different Transcriptional Signals

Although the number of clostridial genes cloned and sequenced has increased dramatically in the last 5 years or so (Minton et al. (1992) "Obligate anaerobes," In: *MOLECULAR BIOLOGY AND BIOTECHNOLOGY O EXTREMOPHILES* 281–320 (Blackies Publishing, Herbert, R. A., J Sharp, eds. 1992), the number of promoters analyzed remains small. Furthermore, there have been no quantitative studies of promoter strength. In order to compare the efficiency with which a selection of clostridial promoters, compared to that of the Fd gene, direct the expression of uidA and ntr, promoters are isolated by PCR, using oligonucleotide primers based on published sequences, and inserted into pMTL500F in place of the Fd promoter. Since ribosomal RNA (rRNA) operons are generally transcribed efficiently, their promoters are a principle target. The necessary genes have been detected in a previously constructed (Oultram et al. (1988) *FEMS Microbiol. Letts.* 56:83–88) gene bank and are currently being characterized. A second promoter is found 5' to ORF C' of the *C. butyricum* plasmid pCB101 (Brehm et al. (1992) *Plasmid* 28:1–13) which exactly conforms to the Gram-positive promoter consensus sequence PATENT (Graves, M. C. and J. C. Rabinowitz (1986) *J. Biol. Chem*. 261:11409–11415). The efficiency with which the two genes are expressed is estimated on the basis of mRNA production, in addition to levels of recombinant protein produced.

(b) Effect of Ribosome Binding Sites

In addition to transcriptional factors, the efficiency with which mRNA transcripts are translated can dramatically effect the levels of product obtained. The relative efficiency of selected RBS sequences is assessed. A previously constructed a modified version of the Fd promoter in which its RBS is flanked by restriction sites (Hpa1 and Nde1) is utilized. This allows substitution of the Fd RBS with the RBS sequences of other genes. Sequences utilized are those which most closely complement the clostridial 16S RNA sequence. They are isolated, by PCR, when a mutagenic primer is used to introduce an Nde1 site at the translational start codon. The presence of this site subsequently allows the precise positioning of the uidA and utr genes. The efficiency of each Fd::RBS variant is assessed with regard to level of mRNA and protein produced (estimated enzymically and by densitometric analysis of total protein).

Example 8

Synthesis and Physico-chemical Evaluation of β-glucuronides of Epirubicin, 5-Fluorouracil and 4-Hydroxycyclophosphamide The β-glucuronides of epirubicin (Acton, E. M. and G. L. Tong (1981) *J. Med. Chem*. 24:669–673), 5-fluorouracil (Alexander et al. (1991) *Tetrahedron Lett*. 32:3269–3272) and 4-hydroxycyclophosphamide (Anlezark et al. (1992) *Biochem. Pharmacol*. 44:2289–2295) are synthesized (see Schemes 1–3).

Haisma (Haisma et al. (1992) *Br. J. Cancer* 66:474–478) showed that epirubicin-β-glucuronide was 100-fold less toxic to human breast and ovarian cancer cells, but became equally toxic as epirubicin when combined with the MAb-β-glucuronidase conjugate. However, they obtained the epirubicin-glucuronide by purification from the urine of patients treated with epirubicin. Epirubicin-β-glucuronide is synthesized by chemical means.

5-Fluorouracil, an antimetabolite, has been in clinical use since 1957. Sensitive tumors include breast cancer, gastrointestinal malignancies, and cancers of the head and neck. Topical administration is useful for basal cell carcinomas and other malignant dermatoses (11). Metabolism of 5-fluorouracil produces two critical intermediates: fluorouridine-5'-phosphate (FUTP), which is incorporated into RNA and interferes with its function, and fluorodeoxyuridylate (FdUMP) which prevents normal DNA replication-(5). The 1-N-β-glucuronide of 5-fluorouracil is synthesized (Alexander et al. (1991) *Tetrahedron Lett.* 32:3269–3272; Kulinkovich, L. N. and V. A. Timoshchuk (1983) Obshch. Khim. 53:1649–1651) and is stable, in vivo (Germane, S. and A. Zidermane (1987) *Eksp. Klin. Farmakoter* 16:36–44) and cleaved to 5-fluorouracil by β-glucuronidase.

Cyclophosphamide is a highly effective and extensively used alkylating agent that possesses a remarkably broad spectrum of activity, demonstrating activity against lymphoma, leukemia, breast cancer, lung cancer, prostate cancer, and ovarian cancer (Black, D. J. and R. B. Livingston (1990) "Antineoplastic drugs in 1990" A Review (Part I) *Drugs* 39:489–501). Activation of cyclophosphamide is initiated by hepatic P450 hydroxylation to produce one or both isomers of 4-hydroxycyclophosphamide (Borch et al. (1984) *J. Med. Chem.* 27:490–494). The 4-hydroxy compound then decomposes via aldophosphamide to generate the active alkylating metabolite, phosphoramide mustard. The novel 4-β-glucuronide of 4-hydroxycyclophosphamide is synthesized.

The synthesis of the β-qlucuronides will be carried out as outlined in Schemes 1–3 below

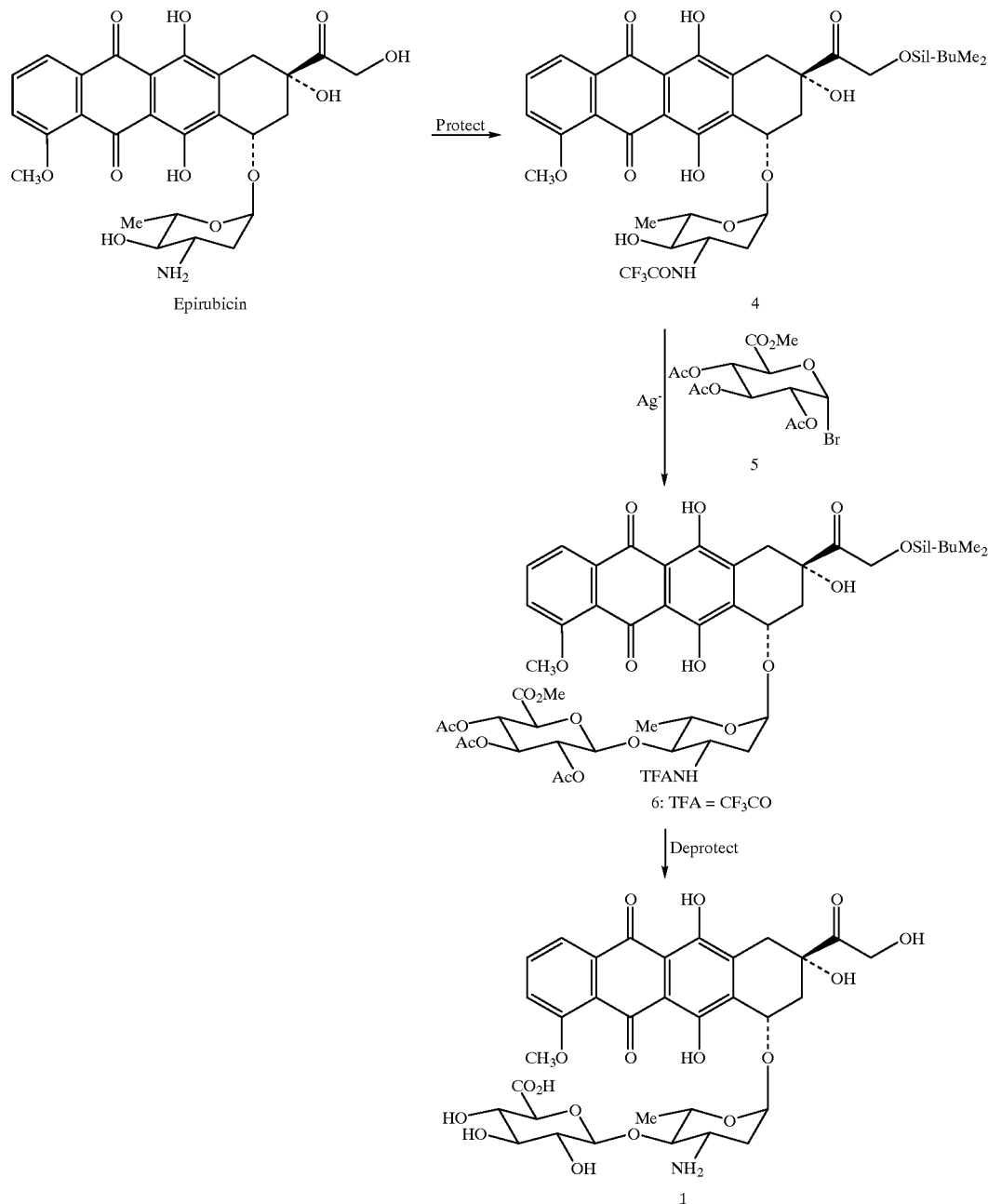

Scheme 2

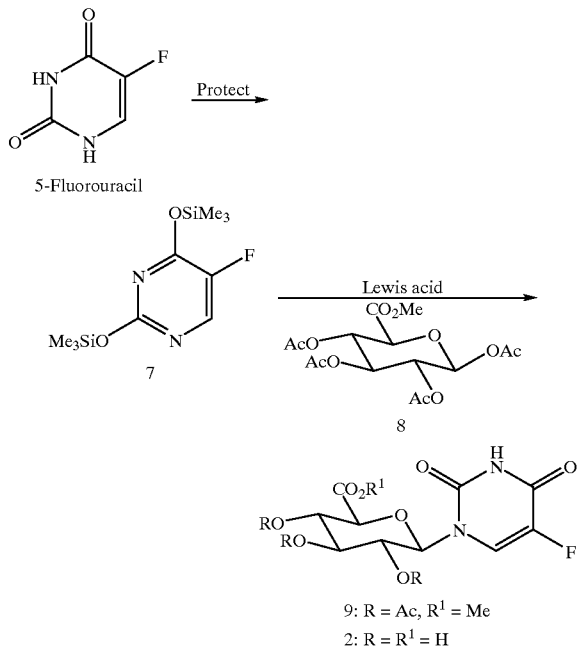

9: R = Ac, R¹ = Me
2: R = R¹ = H

Scheme 3

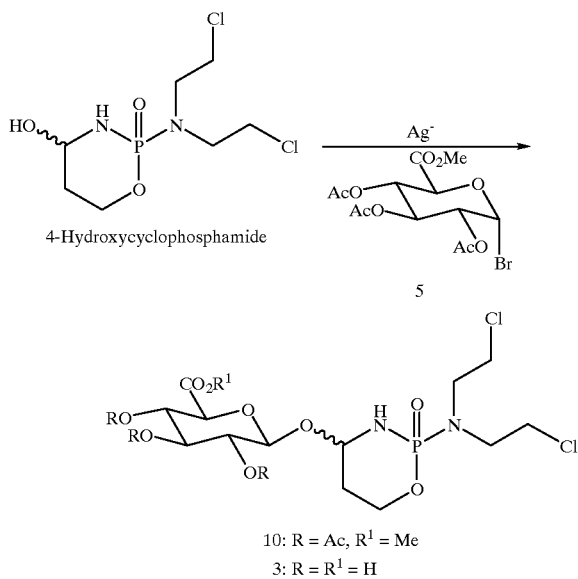

10: R = Ac, R¹ = Me
3: R = R¹ = H

In each example the appropriate aglycone is coupled to either methyl 1-α-bromo-1-deoxy-2,3,4-tri-O-acetyl-$_b$-D-glucopyranuronate (Ardalan, B. and R. Glazer (1981) *Cancer Treat. Rev.* 8:157–167; Bollenback et al. (1955) *J. Amer. Chem. Soc.* 77:3310–3315) or methyl 1,2,3,4-tetra-O-acetyl-β-D-glucopyranuronate (Beguin et al. (1985) *J. Bacteriol.* 162:102–10; commercially available). Neighboring group participation by the acetoxy group in the 2-position results in stereoselective formation of the desired β-glycoside (Binkley, R.).

Sequential protection of the 3'-amino group of epirubicin as the trifluoroacetamide (S-ethyltrifluorothioacetate and the 14-hydroxyl group as the t-butyl-dimethylsilyl ether (t-butyldimethylsilylchloride, imidazole, dimethylformamide; yields 4 (Scheme 1). Coupling of 4 with methyl 1-α-bromo-1-deoxy-2,3,4-tri-O-acetyl-β-D-glucopyranuronate in a Koenigs-Knorr reaction using a silver (I) salt and base yields the protected 4'-β-glucuronide. Removal of the 3'-trifluoroacetamide and 14-silyl ether with TFA and base-catalyzed hydrolysis of the esters yields 1.

The di-trimethylsilyl ether of 5-fluorouracil is synthesized using hexamethyl-disilazane under anhydrous conditions (Scheme 2). Coupling with methyl 1,2,3,4-tetra-O-acetyl-β-D-glucopyranuronate in the presence of boron trifluoride etherate yields two β-glucuronides, the desired product and the 3-isomer. Isolation of 9 by chromatography and base-catalyzed hydrolysis yields the 1-β-glucuronide.

Coupling of 4-hydroxy-cyclophosphamide (Takamizawa et al. (1975) *J. Med. Chem.* 18:376–383) with methyl 1-A-bromo-1-deoxy-2,3,4-tri-O-acetyl-β-D-glucopyranurona in a Koenigs-Knorr reaction as described above yields the protected 4-β-glucuronide directly. Base-catalyzed hydrolysis will give 3.

For each β-glucuronide conjugate the key physicochemical properties (ultraviolet spectrum, solubility, partition coefficient, and pKa) are measured. HPLC assays are developed for each conjugate, to enable analysis of stability in various media and determination of kinetics for the hydrolysis of the conjugates by β-glucuronidase to give the active drug and/or key metabolites.

METHODS

Mice and Tumors

The mice used in this investigation are either C3H/Km (for transplantation of the RIF-1 and SCCVII/St mouse tumors), BALB/c (for transplantation of the EMT6/St tumor) or SCID mice (for transplantation of the HT 29 human tumor). Normal tissue studies are performed on C3H/Km mice. All the mice are bred and housed in our own mouse rooms within the new Research Animal Facility at Stanford. All the tumors are assayed for cell survival in vitro by plating single cells into petri dishes.

Rodent tumors have been used extensively over the past 5–20 years (depending on the tumor), and rigorous procedures have been established for passage of the cells from frozen tumor characteristics. A full description of this is given for the RIF-1 tumor (Twentyman et al. (1980) *J. Natl. Cancer Inst.* 64:595–604), and an identical practice is used for the other tumors. Full descriptions of the derivation, characteristics and handling of the rodent tumors have been published (see for example, Brown et al. (1979) *J. Natl. Cancer Inst.* 64:605–611; Brown et al. (1981) *Int. J. Radiat. Oncol. Biol. Phys.* 7:695–703; Hirst et al. (1982) *Br. J. Cancer* 46:109–116; Rockwell et al. (1972) *J. Natl. Cancer* 49:735–749). The HT 29 cells were obtained form the American Type Culture Collection (ATCC) (Rockville, Md.) and are maintained in Alpha MEM+10% fetal bovine serum.

In Vivo-In Vitro Excision Assay

The excision assay is performed on all the tumors used in these studies. This assay is extremely reliable and allows detailed comparisons to be made of different radiosensitizers and fractionation regimens (Brown, J. M. and M. J. Lemmon (1990) *Cancer Res.* 50:7745–7749; Brown, J. M. and M. J. Lemmon (1991) *Oncol. Biol. Phys.* 20:457–461; Brown et al. (1979) *J. Natl. Cancer Inst.* 64:605–611; Brown, J. M. and N. Y. Yu (1980) *Br. J. Radiol.* 53:915–916; Brown et al. (1981) *Int. J. Radiat. Oncol. Biol. Phys.* 7:695–703; Stone et al. (1991) *Int. J. Radiat. Oncol. Biol. Phys.* 20:987–995)

Regrowth Delay Assay

This assay is performed on the SCCVII/St, RIF-1, and the HT 29 tumors. After treatment, tumor volumes are measured three times weekly. For each mouse, the time required for its tumor to regrow to a size equal to 2 or 4 times the tumor volume at the time of treatment is determined and a geometric mean value (± standard error) for each group calculated. The regrowth delay is this value. This delay is then plotted as a function of the dose for each treatment group. (Brown, J. M. (1975) *Radiat. Res.* 64:633–647; Brown, J. M. and D. G. Hirst (1982) *Br. J. Cancer* 45:700–708; Brown, J. M. and M. J. Lemmon (1990) *Cancer Res.* 50:7745–7749; Brown et al. (1979) *J. Natl. Cancer Inst.* 64:605–611; Stone et al. (1991) *Int. J. Radiat. Oncol. Biol. Phys.* 20:987–995).

Tumor Control ($TCD_{50}$) Assay

For some experiments, the dose to produce tumor control is used in 50% of the treated mice (the $TCD_{50}$) as the endpoint. After treatment the tumors are measured weekly until they exceed 4× the treatment volume or reach 120 days post-treatment. At this time, the mice are sacrificed and autopsied. A mouse is recorded as "cured" if at 120 days post-treatment it does not have a tumor greater than 4 mm mean diameter. $TCD_{50}$ values and 95% confidence intervals are obtained using a computer program which fits the data using a probit transform. This assay has been used in testing the MDAH/MCa4 carcinoma and RIF-1 sarcoma (Brown, J. M. and N. Y. Yu (1981) *Int. J. Radiat. Oncol. Biol. Phys.* 7:695–703; Brown et al. (1979) *J. Natl. Cancer Inst.* 64:605–611; Stone et al. (1991) *Int. J. Radiat. Oncol. Biol. Phys.* 20:987–995) and is used with the SCCVII and RIF-1 mouse tumors and the HT 29 human tumor.

White Blood Cell Counts

This assay is used to evaluate the systemic effect of the chemotherapeutic drugs. It has been used extensively in studies with alkylating agents and nitroimidazoles (Brown, J. M. and D. G. Hirst (1982) *Br. J. Cancer Res.* 45:700–708; Hirst et al. (1984) *Int. J. Radiat. Biol.* 46:345–354; Hirst et al. (1985) *Int. J. Radiat. Oncol. Biol. Phys.* 11:1349–1355). Blood samples (5 µl) are taken from the tail at predetermined times during and following treatment. The sample is diluted in 2% glacial acetic acid to lyse the erythrocytes and the resulting cell suspension counted in a hemacytometer. The results are expressed as the number of leucocytes per $mm^3$ of blood. At least five mice per treatment group are used.

Measurement of Tumor Hypoxia and Necrosis (a) Radiobiological Assay: The percent hypoxic cells in tumors is conveniently estimated using the paired survival curve method with clamped tumors and tumors in air-breathing, nonanesthetized mice (Kallman, R. F. (1972) *Radiology* 105:135–142). This assay has been used most recently in evaluating the effect or prior irradiation of the tumor transplantation site on tumor hypoxia (Kim et al. (1993) *Radiat. Res.* 135:411–417). Tumors are implanted ($5 \times 10^5$ cells intradermally) on the dorsum near the base of the tail and are irradiated locally using a 250 kVp X-ray machine. Unanesthetized mice are placed in lead boxes through which the tumors protrude for irradiation. The irradiation procedures and characteristics of the boxes and clamps (for hypoxic irradiation) have been published elsewhere (Brown, J. M. and M. J. Lemmon (1990) *Cancer Res.* 50:7745–7749; Brown, J. M. and N. Y. Yu (1984) *Int. J. Radiat. Oncol. Biol. Phys.* 10;1207–1212). Briefly, however, the dose rate is 1.69 Gy/min with added filtration of 0.35 mm copper, 15 mA, target to tumor distance of 31 cm and a half value layer of 1.3 mm copper.

(b) $^3$H-MISO Binding: The binding of $^3$H-Misonidazole is used as an independent measure of the level of tumor hypoxia in non-necrotic tissue. Tumor-bearing mice are given an i.p. injection of 0.1 µCi/g of $^3$H-MISO. One day after injection, the tumors are excised, solubilized in Protosol for 24 hr at 50° C. then counted in Aquasol in a scintillation counter. It has been previously shown that the amount of $^3$H-MISO bound correlates well with changes in the radiobiologically hypoxic fraction after manipulations (Hirst et al. (1984) *Int. J. Radiat. Oncol. Biol. Phys.* 46:345–354; Hirst et al. (1985) *Int. J. Radiat. Oncol. Biol. Phys.* 11:1349–1355; Kim et al. (1993) *Radiat. Res.* 135:411–417).

(c) Oxygen Electrode Measurements: A profile of oxygen concentration in a single tumor is obtained using the Eppendorf $pO_2$ histograph. Details of the use and results obtained from this are published (Kim et al. (1993) *Radiat. Res.* 135:411–417). Briefly, however, 30 to 60 individual oxygen measurements are made by inserting the electrode through 4 to 8 different tracts through the tumor.

A major benefit of this technique is that it provides a profile of oxygen tension of the tumor which is independent of cell viability (as opposed to the radiobiological and $^3$H-MISO binding assays). In other words, it measures oxygen levels in both viable tumor tissue and in tumor necrosis. This assay is also the only one that gives absolute values of tumor oxygenation, which is important for evaluating oxygen measurements from human tumors to determine whether proliferation of *C. acetobutylicum* is likely in these tumors.

Growth of *C. Acetobutylicum*

*C. acetobutylicum* are routinely grown in an anaerobic chamber in 2X YTG media (1.6% tryptone, 1% yeast extract, 0.5% glucose, and 0.5% NaCl) or on plates of 2X YTG containing 1.5% agar. Media is brought quickly into the anaerobic chamber after autoclaving (which drives off the dissolved oxygen) and is then equilibrated with the chamber atmosphere for 24 hrs before use. The bacteria are normally grown at 37° C. unless sporulation cultures are in progress in the same incubator; in which case, the temperature is reduced to 30° C. The bacteria grow equally well at these two temperatures with a doubling time of 45–60 min.

Sporulation Procedure for *C. Acetobutylicum* NCIB 8052

Sporulation cultures are started from exponentially growing cultures with an optical density at 600 nm of 0.45. Cultures are set up containing 2% bacteria in Cooked Meat Media (Difco Laboratories, Detroit) from which the undissolved pellets are removed. This increases sporulation and makes the cultures more suitable for injection into mice. Cultures are incubated at a suboptimal growth temperature of 30° C. for about one week, after which maximum sporulation (usually 40–60%) is obtained. The spores are then washed 3× with PBS and subjected to an 80° C. 20 min heat shock (1 ml volume). This heat shock serves several purposes—it kills all vegetative rods, enabling a more accurate spore count to be obtained (by plating the bacteria) than can be obtained from the counts under the microscope, it confirms that spores are present, and it activates the spores to return to the vegetative form. Spores are then stores at −20° C. until needed for animal injection. Spores are injected intravenously into mice in 0.1 ml volume from spore suspensions in PBS of $10^9$ spores/ml.

Nitroreductase Activity Assay

Nitroreductase activity is measured in *C. acetobutylicum* cultures using a modification of the method developed by Gordon et al. (1991) *Carcinogen* 12:2393–2396 to measure DT diaphorase activity. Briefly, samples diluted in 25 mM Tris-HCl buffer containing 0.7 mg/ml bovine serum albumin are placed in an assay mixture containing 4 µM dichlorophenol-indophenol (DCIP) and 200 μM NADH, and the rate of DCIP reduction is followed spectrophotometrically at 600 nm. Replicate samples containing 50 μM dicoumoral, a potent inhibitor of nitroreductase, are used to correct for nonspecific DCIP reduction. One unit of activity is defined as the reduction of 1 μmol of DCIP per min. Activity values are normalized by sample protein content. Protein concentrations are measured with a BCA Protein Assay Kit method (Pierce) utilizing bovine serum albumin as a standard.

Detection of Nitroreductase Activity by Native Polyacrylamide Gel Electrophoresis Nondenaturing polyacrylamide gel electrophoresis is performed by the method of Davis using 10% slab gels in a Bio-Rad Mini-Protein II apparatus (Davis, J. B. (1964) *Annals N.Y. Acad. Sci.* 121:404–407). Nitroreductase activity is visualized by a modification of the method of Kaplan and Beutler used to measure glutathione reductase (Kaplan, J. C. and E. Beutler (1968) *Nature* 217:256–261). When oxidized glutathione is omitted from the assay mixture, this method detects both DT diaphorase and nitroreductase. These two enzymes are easily differentiated by their dramatically different electrophoretic mobilities.

HPLC Assay of CB 1954 Metabolites

The HPLC assay of Knox et al. is used to measure the CB 1954 reduction in plasma and tumor homogenates (Knox et al. (1988) *Biochem. Pharmacol.* 37:4661–4669).

Polyclonal Antibody Production

Antibody against NTR is used for both immunoassays and immunohistochemistry to visualize the localization of expressed recombinant nitroreductase in tumor and tissue slices. An antibody to crude whole-clostridia homogenate is produced. This antibody is used with immunohistochemistry methods to augment traditional staining methods designed to detect both vegetative and spore forms of clostridia in tissue and tumor sections. Polyclonal antibodies for use in immunohistochemistry, immunoblotting, and ELISA assays are produced in rabbits using a modification of the technique published by Oberley et al. (1990) *Amer. J. Pathol.* 137:199–214. Due to the bacterial origin of the antigens, prior to immunization, the antigen preparations are rendered endotoxin-free by passing them over a lipid A-binding affinity matrix (Detoxi-Gel, Pierce). This procedure also utilizes Ribi adjuvant instead of Freund's complete and incomplete adjuvant to minimize animal discomfort.

Electrophoresis and Immunoblotting

SDS-PAGE one dimensional electrophoresis are carried out in 12% gels as described by Laemmli, U. K. (1970) *Nature* 227:680–685. Following electrophoresis, protein is transferred to nitrocellulose sheets using a Bio-Rad semi-dry blotter at 25 V for 1 hr using the buffer system of Towbin et al. (1979) *Proc. Natl. Acad. Sci. USA* 76:4350–4354. Immunobiotting is performed using anti-*E. coli* nitroreductase polyclonal antibody raised in rabbits.

ELISA Assays for Clostridial Proteins

Levels of nitroreductase and clostridial cell wall protein are quantified in tumor tissue, plasma, and normal host tissue using the ELISA technique. In order to maximize the-sensitivity of the assay, the non-competitive homogeneous sandwich ELISA assay of Noe et al. (1992) *Brit. J. Haem.* 80:285–292 is used. Briefly, rabbit polyclonal antibodies raised against purified *E. coli* nitroreductase or clostridial cell wall extract is adsorbed onto 96-well plates. Serially diluted samples of plasma, cell lysates, or standards consisting of *E. coli* nitroreductase protein are then added to the wells. After allowing for the antigen to bind to the immobilized antibody, the wells are washed repeatedly to remove unbound protein. Biotinylated anti-*E. coli* nitroreductase polyclonal antibody is then added to the well and allowed to react with the immobilized antigen. Avidin and biotinylated alkaline phosphatase are then added, the wells are washed, and the signal quantified by adding p-nitrophenyl phosphate and reading the absorbance at 405 nm using a 96-well plate reader.

β-Glucuronidase Activity Assay

β-glucuronidase activity is measured by the spectrophotometric method described by Fishman, W. H., "β-Glucuronidase" In: *METHODS OF ENZYMATIC ANALYSIS* (Weinheim: Verlag Chemie, Bergmeyer, H. U. and K. Gawehn, eds. 1974). Plasma or crude cell homogenates are incubated in acetate buffer pH 4.0 with 8 mM 4-nitrophenyl-β-D-glucuronoside and monitored continuously at 405 nm for the release of 4-nitrophenol ($\epsilon_{405}$=18.5 $mmol^{-1}cm^{-1}$). The slope of the absorbance curve is used to calculate enzymatic activity. One unit of β-glucuronidase activity is defined as the release of 1 umol 4-nitrophenol per min at 25 C and pH 4.0.

We claim:

1. A method of targeting a toxic chemotherapeutic agent to a tumor in a tumor-bearing individual comprising the steps of:

(a) administering an effective amount of a genetically engineered nonpathogenic anaerobic microorganism which proliferates and produces an enzyme in the hypoxic/necrotic environment of a tumor to said individual; and then (b) systemically administering a prodrug which is converted at the site of the tumor to the toxic chemotherapeutic agent by the enzyme produced by the microorganism, wherein the enzyme is nitroreductase.

2. The method of claim 1, wherein the prodrug is CB1954.

3. The method of claim 1, wherein the anaerobic microorganism is *clostridium acetobutylicum*, the enzyme is *E. coli* B nitroreductase (NTR) and the prodrug is CB1954.

* * * * *

UNITED STATES PATENT AND TRADEMARK OFFICE
CERTIFICATE OF CORRECTION

PATENT NO. : 6,416,754 B1  Page 1 of 1
DATED : July 9, 2002
INVENTOR(S) : Brown et al.

Figure 5:
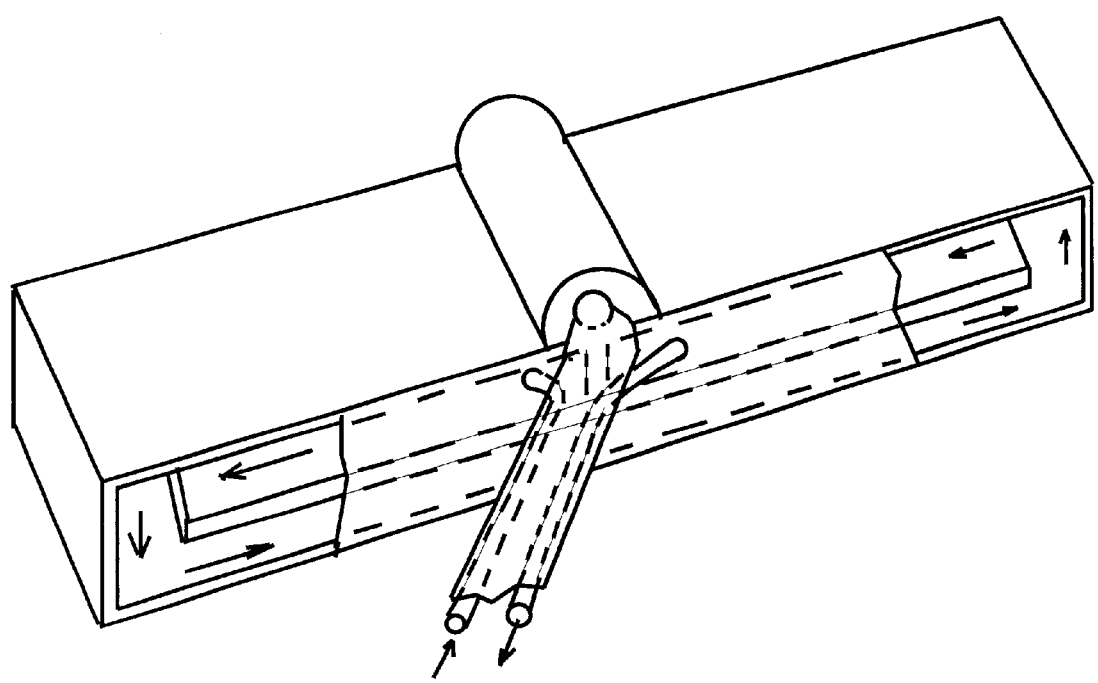
FIGS. 5A and 5B illustrate the detection of recombinant NTR activity and protein in tumor homogenates.

It is certified that error appears in the above-identified patent and that said Letters Patent is hereby corrected as shown below:

Drawings,
Sheet 5, Fig. 5 should be replaced as follows:

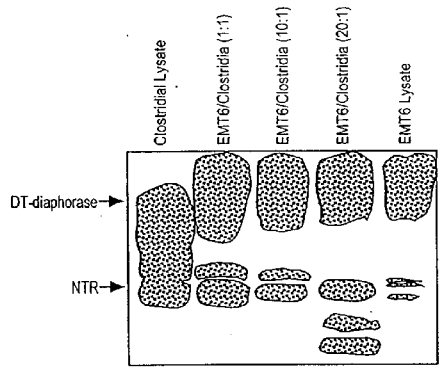
Fig. 5A

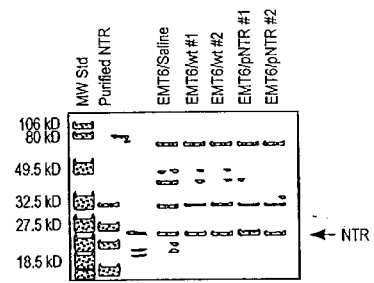
Fig. 5B

Signed and Sealed this

Twelfth Day of November, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 6,416,754 B1
DATED : July 9, 2002
INVENTOR(S) : Brown et al.

It is certified that error appears in the above-identified patent and that said Letters Patent is hereby corrected as shown below:

<u>Title page,</u>
Item [22], should read as follows:
-- [22] Filed: July 23, 1996 --

Signed and Sealed this

Seventeenth Day of August, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,416,754 B1
DATED : July 9, 2002
INVENTOR(S) : John Martin Brown, Nigel P. Minton and Amato Giaccia It is certified that error appears in the above-identified patent and that said Letters Patent is hereby corrected as shown below:

<u>Column 1,</u>
Line 12, please insert the following paragraph:
-- This work was supported in part by The National Institutes of Health Grant CA 15201. Accordingly the United States government may have certain rights in this invention. --

Signed and Sealed this

Fourteenth Day of December, 2004

JON W. DUDAS
*Director of the United States Patent and Trademark Office*